United States Patent [19]

Moltzen et al.

[11] Patent Number: 6,140,331

[45] Date of Patent: *Oct. 31, 2000

[54] FUSED BENZO COMPOUNDS FOR THE TREATMENT OF CENTRAL NERVOUS SYSTEM DISORDERS

[75] Inventors: Ejner K. Moltzen, Gentofte; Jens Perregaard, Jægerspris; Henrik Pedersen, Broenshoej, all of Denmark

[73] Assignee: H. Lundbeck A/S, Copenhagen-Valby, Denmark

[ * ] Notice: This patent issued on a continued prosecution application filed under 37 CFR 1.53(d), and is subject to the twenty year patent term provisions of 35 U.S.C. 154(a)(2).

[21] Appl. No.: 08/998,245

[22] Filed: Dec. 24, 1997

Related U.S. Application Data

[62] Division of application No. 08/504,846, Jun. 6, 1995, Pat. No. 5,753,661, which is a continuation of application No. PCT/DK93/00414, Dec. 8, 1993.

[30] Foreign Application Priority Data

Dec. 9, 1992 [DK] Denmark .................. 1483/92

[51] Int. Cl.$^7$ ............... A61K 31/445; A61K 31/495; C07D 405/04; C07D 405/14

[52] U.S. Cl. ............... 514/254.07; 514/320; 514/337; 544/368; 544/370; 544/376; 544/377; 546/196; 546/199; 546/273.7; 546/274.4; 546/282.7; 546/283.1; 546/284.1

[58] Field of Search .................. 514/254, 320, 514/337, 254.07; 544/368, 370, 376, 377; 546/196, 199, 273.7, 274.4, 282.7, 283.1, 284.1

[56] References Cited

U.S. PATENT DOCUMENTS

| | | | |
|---|---|---|---|
| 4,216,216 | 8/1980 | Weber et al. | 424/251 |
| 4,302,592 | 11/1981 | Teiman | 548/144 |
| 4,506,078 | 3/1985 | Batcho | 548/469 |
| 4,831,031 | 5/1989 | Lowe, III et al. | 514/254 |
| 4,950,670 | 8/1990 | Frost et al. | 514/254 |
| 5,424,313 | 6/1995 | Hartog et al. | 514/254 |
| 5,439,922 | 8/1995 | Perregaard et al. | 514/323 |

FOREIGN PATENT DOCUMENTS

| | | |
|---|---|---|
| 0 138 280 | 4/1985 | European Pat. Off. . |
| 0 147 044 | 7/1985 | European Pat. Off. . |
| 0 185 429 | 6/1986 | European Pat. Off. . |
| 0 281 309 | 9/1988 | European Pat. Off. . |
| 0 343 050 | 11/1989 | European Pat. Off. . |
| 0 364 327 | 4/1990 | European Pat. Off. . |
| 0 372 657 | 6/1990 | European Pat. Off. . |
| 0 376 607 | 7/1990 | European Pat. Off. . |
| 0 466 585 | 1/1992 | European Pat. Off. . |
| 0 490 772 | 6/1992 | European Pat. Off. . |
| 0 526 434 | 2/1993 | European Pat. Off. . |
| 2035370 | of 1971 | Germany . |
| 3526510 | of 1986 | Germany . |
| 1 456 253 | 11/1976 | United Kingdom . |
| WO 92/03426 | 3/1992 | WIPO . |

OTHER PUBLICATIONS

D.E. Boswell et al., *Journal of Heterocyclic Chemistry* (1968), vol. 5, No. 1, pp. 69–75.

Eric F.V. Scriven et al., *Journal of the Chemical Society*, Perkins Transactions 1 (1979), pp. 53–59.

L. Lee Melhado et al., *Journal of Organic Chemistry* 48 (1983), pp. 5130–5133.

Mark D. Tricklebank et al., *European Journal of Pharmacology* (1985), vol. 117, pp. 15–24.

Torben Skarsfeldt et al., *European Journal of Pharmacology* (1986), vol. 125, pp. 333–340.

Mark D. Tricklebank et al., *European Journal of Pharmacology* (1987), vol. 133, pp. 47–56.

Ineke van Wijngaarden et al., *Journal of Medicinal Chemistry* (1988), vol. 31, pp. 1934–1940.

C.G. Kruse et al., *Recueil des Travaux Chimiques des Pays–Bas* (1988), vol. 107, No. 4, pp. 303–309.

Luigi Cervo et al., *European Journal of Pharmacology* (1988), vol. 158, pp. 53–59.

(List continued on next page.)

*Primary Examiner*—Mukund J. Shah
*Assistant Examiner*—Brenda Coleman
*Attorney, Agent, or Firm*—Darby & Darby

[57] ABSTRACT

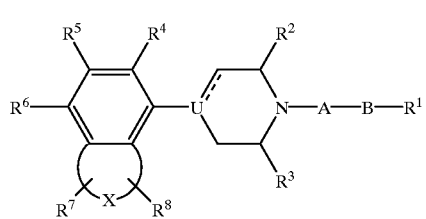

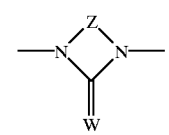

Fused benzo compounds of formula (I), wherein A is a 2 to 6 membered hydrocarbon spacer group, B is a polar divalent group selected from SO, $SO_2$, and a group (a); U is C, N or CH; X is a divalent 3–4 membered chain optionally comprising one or more heteroatoms; $R^1$ is an aliphatic hydrocarbon group, arylalkyl or diphenylalkyl; $R^2$ and $R^3$ are hydrogen or alkyl or together form an ethylene or propylene bridge; $R^4$, $R^5$ and $R^6$ are hydrogen or substituents; $R^7$ and $R^8$ are hydrogen or substituents including, a group —$COOR^9$ and a group —$CONR^{10}R^{11}$; are 5-$HT_{1A}$ receptor ligands useful in the treatment of CNS disorders. Pharmaceutical compositions comprising the compounds and their use for the manufacture of a pharmaceutical preparation are also disclosed.

9 Claims, No Drawings

OTHER PUBLICATIONS

Richard A. Gillis et al., *The Journal of Pharmacology and Experimental Therapeutics* (1988), vol. 248, No. 2, pp. 851–857.

Gregory E. Martin et al., *Journal of Medicinal Chemistry* (1989), vol. 32, pp. 1052–1056.

Debra A. Glitz et al., *Drugs* (1991), vol. 41, No. 1, pp. 11–18.

Jochen H.M. Prehn et al., *European Journal of Pharmacology* (1991), vol. 203, pp. 213–222.

A. van Hest et al., *Psychopharmacology* (1992), vol. 107, pp. 474–479.

Connie Sanchez et al., *Psychopharmacology* (1993), vol. 110, pp. 53–59.

Boddeke, Henrikus W.G.M. et al., "Agonist/antagonist interactions with cloned human 5-$HT_{1A}$ receptors: variations in intrinsic activity studied in transfected HeLa cells," *Naunyn–Schmiedeberg's Arch. Pharmacol.*, (1992), 345(3)257–63 (abstract).

Glennon, Richard A. et al., "Arylpiperazine Derivatives as High Affinity 5-$HT_{1A}$ Serotoin Ligands," *Journal of Medical Chemistry*, vol. 31, No. 10 (1988), pp. 1968–1971.

Hyttell, John et al., "Neurochemical Profile In Vitro of Irindalone:A 5-$HT_2$-Receptor Antagonist," *Drug Development Research* 15 (1988), pp. 389–404.

Hyttell, John et al., "Neurochemical Profile of Lu 19–005, a Potent Inhibitor of Uptake of Dopamine, Noradrenaline, and Serotonin," *Journal of Neurochemistry*, vol. 44, No. 5 (1985), pp. 1615–1622.

FUSED BENZO COMPOUNDS FOR THE TREATMENT OF CENTRAL NERVOUS SYSTEM DISORDERS

This is a division, of application Ser. No. 08/504,846, filed Jun. 6, 1995 now U.S. Pat. No. 5,753,661, which is a continuation of International Application Ser. No. PCT/DK93/00414, filed Dec. 8, 1993. Each of these prior applications is hereby incorporated herein by reference, in its entirety.

FIELD OF THE INVENTION

The present invention relates to a class of fused benzoderivatives potently binding to the 5-$HT_{1A}$ receptor and having central serotonergic 5-$HT_{1A}$ activity. These fused benzoderivatives are, therefore, useful in the treatment of certain psychic and neurological disorders.

BACKGROUND OF THE INVENTION

A number of compounds structurally related to the compounds of the invention are known from the prior art.

So, EP patents Nos. 0 138 280 and 0 185 429 disclose an extremely broad class of piperazinyl compounds having a bicyclic hetero aryl radical in the 4-position and a heteroaryl-, aryl- or alkyl substituted carbamoylethyl or carbamoylpropyl group in the 1-position. Said compounds are alleged to show blood pressure lowering effect through a central mechanism. EP 0 372 657 discloses similar derivatives differing only in that they have slightly different substituents on the bicyclic heteroaryl radical. These latter derivatives are said to exert anxiolytic effects in animal models without showing effect on the blood pressure. One of the compounds covered by EP patent No. 0 138 280, i.e. the compound 4-fluoro-N-[2-(4-(2-hydroxymethyl-1,4-benzodioxan-5-yl)piperazine-1-yl)ethyl]benzamide, which is known as flesinoxan has recently been reported to be a high efficacy 5-$HT_{1A}$ agonist having antidepressant and anxiolytic effects (Schipper et al, Human Psychopharm., 1991, 6, S53).

EP patent No 0 364 327 discloses a class of 4-[2-(4-(naphthyl- or isoquinolyl)piperazine-1-yl)ethyl]-2-quinolone derivatives having 5-$HT_{1A}$ and 5-$HT_2$ receptor activity. The compounds are said to be agonists, partial agonists or antagonists in vivo. EP 0 343 050 describes a group of 6-phenyl-3-[(4-(naphthyl or isoquinolyl)piperazine-1-yl)alkyl(2-4)]-1H,3H-pyrimidine-2,4-dione compounds said to posses 5-$HT_{1A}$ and 5-$HT_2$ receptor activity. Again, with respect to the 5-$HT_{1A}$ receptor, the compounds are said to be agonists, partial agonists or antagonists in vivo.

In International patent publication No. WO 92/03426 a class of piperazine derivatives having naphtyl or quinolyl in the 4-position and a N-aryl substituted carbamoyl alkyl group or a N-aryl substituted ureido alkyl group in the 1-position is described. Said compounds are claimed to exhibit affinity for various receptors, including 5-$HT_2$, 5-$HT_{1A}$, alpha and dopamine receptors.

EP patent No 0 466 585 relates to 1-(benzamidoalkyl)-4-(naphthyl- or quinolyl)piperidines or -tetrahydropyridines having 5-$HT_{1A}$ receptor affinity and found to exhibit potent antihypertensive effect in animals.

Finally, EP 0 490 772 A1 discloses a class of 1,4-disubstituted piperazine derivatives alleged to show 5-$HT_{1A}$ antagonistic activitivities. Said derivatives have a 5-benzodioxanyl or 7-isobenzofuranyl radical in the 4-position and a lower alkyl chain substituted with a bicyclic carbo ring system in the 1-position.

Compounds having central serotonergic 5-$HT_{1A}$ activity may according to well known and recognized pharmacological principles be devided into full agonists, partial agonists and antagonists.

Clinical studies of known 5-$HT_{1A}$ partial agonists such as e.g. buspirone (8-[4-[4-(2-pyrimidyl)-1-piperazinyl]butyl]-8-azaspiro[4,5]decane-7,9-dione), ipsapirone (4,4-dimethyl-1-[4-[4-(2-pyrimidyl)-1-piperazinyl]butyl]-2,6-piperidinedione), and gepirone (2-[4-[4-(2-pyrimidyl)-1-piperazinyl]butyl]-1,2-benzothiazol-3(2H)-one-1,1-dioxide), have shown that 5-$HT_{1A}$ partial agonists are useful in the treatment of anxiety disorders such as generalised anxiety disorder, panic disorder, and obsessive compulsive disorder (Glitz, D. A., Pohl, R., Drugs 1991, 41, 11). Preclinical studies indicate that full agonists also are useful in the treatment of the above mentioned anxiety related disorders (Schipper, Human Psychopharm., 1991, 6, S53).

There is also evidence, both clinical and preclinical, in support of the beneficial effect of 5-$HT_{1A}$ partial agonists in the treatment of depression as well as impulse control disorders and alcohol abuse (van Hest, Psychopharm., 1992, 107, 474; Schipper et al, Human Psychopharm., 1991, 6, S53; Cervo et al, Eur. J. Pharm., 1988, 158, 53; Glitz, D. A., Pohl, R., Drugs 1991, 41, 11).

5-$HT_{1A}$ agonists and partial agonists inhibit isolation-induced aggresion in male mice indicating that these compounds are useful in the treatment of aggression (Sanchéz et al, Psychopharmacology, 1993, 110, 53–59).

Furthermore, recent studies also indicate that 5-$HT_{1A}$ receptors are important in the serotonergic modulation of haloperidol-induced catalepsy (Hicks, Life Science 1990, 47, 1609) suggesting that 5-$HT_{1A}$ agonists are useful in the treatment of the side effects induced by conventional antipsychotic agents such as e.g. haloperidol.

5-$HT_{1A}$ agonists have shown neuroprotective properties in rodent models of focal and global cerebral ischaemia and may, therefore, be useful in the treatment of ischaemic disease states (Prehn, Eur. J. Pharm. 1991, 203, 213).

Pharmacological studies have been presented which indicates that 5-$HT_{1A}$ antagonists arm useful in the treatment of senile dementia (Bowen et al, Trends Neur. Sci. 1992, 15, 84).

Both in animal models and in clinical trials it has been shown that 5-$HT_{1A}$ agonists exert antihypertensive effects via a central mechanism (Saxena and Villalaón, Trends Pharm. Sci. 1990, 11, 95; Gillis et al, J. Pharm. Exp. Ther. 1989, 248, 851. 5-$HT_{1A}$ ligands may, therefore, be beneficial in the treatment of cardiovascular disorders.

Accordingly, agents acting on the 5-$H_{1A}$ receptor, both agonists and antagonists, are believed to be of potential use in the therapy of such conditions and thus being highly desired.

It has now been found that compounds of a certain class of fused benzoderivatives bind to the 5-$HT_{1A}$ receptor with high affinities. Furthermore, it has been found that the compounds cover a broad range of selectivities for the 5-$HT_{1A}$ receptor vs. the dopamine $D_2$ receptor and the $alpha_1$ adrenoceptor and a broad range of the efficacy scale.

SUMMARY OF THE INVENTION

Accordingly, the present invention provides a novel class of fused benzo compounds of the general Formula I

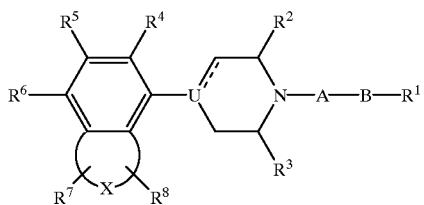

I wherein A is a 2 to 6 membered spacer group selected from alkylene, alkenylene, and alkynylene each of which may be branched or straight chain, or a 3–7 membered cycloalkylene group, said spacer group being optionally substituted with aryl or hydroxy;

B is a polar divalent group selected from SO, SO$_2$, and a group of Formula II,

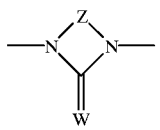

II wherein W is O or S, and Z is selected from —(CH$_2$)$_n$— n being 2 or 3, —CH=CH—, —COCH$_2$—, —CSCH$_2$—, or 1,2-phenylene optionally substituted with halogen or trifluoromethyl;

U is N or CH; the dotted line designates an optional bond, and if it designates a bond U is C;

X is selected from the group of divalent 3–4 membered groups consisting of

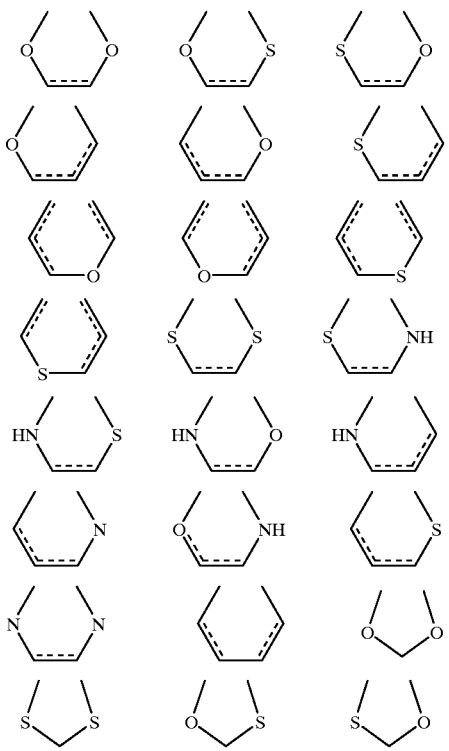

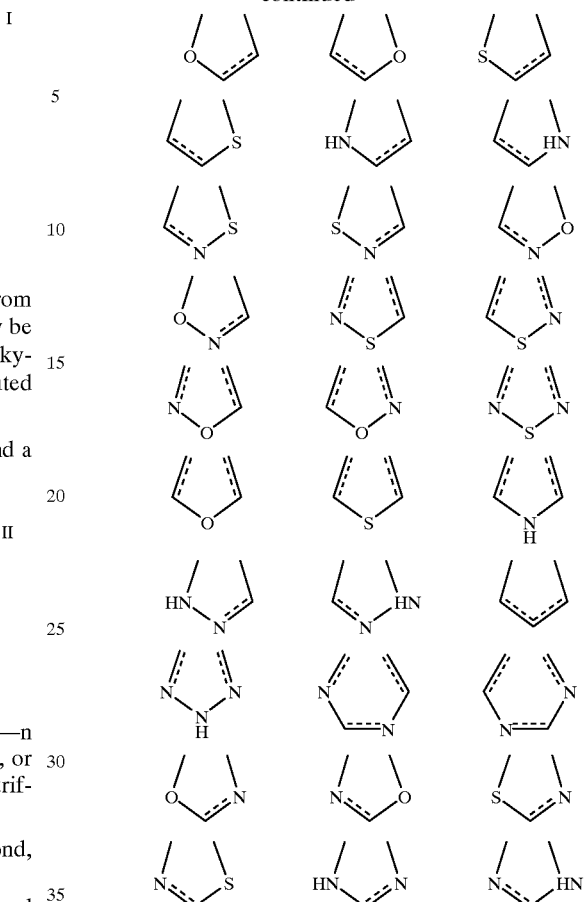

wherein the dotted lines indicate optional bonds; thereby forming a carbocyclic or heterocyclic ring fused with the benzene ring;

$R^1$ is alkyl, alkenyl, cycloalk(en)yl, aryl, cycloalk(en)ylalk(en/yn)yl, arylalkyl, diphenylalkyl, any alkylgroup optionally being substituted with one or two hydroxy groups, with the proviso that if Z is 1,2-phenylene and U is N, then $R^1$ is selected from aryl and substituted aryl;

$R^2$ and $R^3$ are independently hydrogen, lower alkyl or they may be linked together, thereby forming an ethylene or propylene bridge;

$R^4$, $R^5$, and $R^6$ are independently selected from the group consisting of hydrogen, halogen, lower alkyl, lower alkoxy, hydroxy, lower alkylthio, lower alkylamino or di-lower-alkylamino, cyano, nitro, trifluoromethyl and trifluoromethylthio;

$R^7$ and $R^8$ are independently selected from the group consisting of hydrogen, halogen, trifluoromethyl, lower alkyl, lower alkyl substituted with one or more hydroxy groups, aryl, cyano, a group —COOR$^9$ and a group —CONR$^{10}$R$^{11}$, R$^9$, R$^{10}$, and R$^{11}$ being hydrogen or lower alkyl; any aryl group present being optionally substituted with one or more substituents selected from halogen, lower alkyl, lower alkoxy, hydroxy, lower alkylthio, lower alkylsulfonyl, lower alkyl- or dialkylamino, cyano, trifluoromethyl, or trifluoromethylthio;

and pharmaceutically acceptable acid addition salts thereof.

In a second aspect the present invention provides a pharmaceutical composition comprising at least one novel fused benzoderivative according to the invention as defined above or a pharmaceutically acceptable acid addition salt thereof or prodrug thereof in a therapeutically effective amount and in combination with one or more pharmaceutically acceptable carriers or diluents.

In a further aspect the present invention provides the use of fused benzoderivatives having the above defined general Formula I or acid addition salts or prodrugs thereof for the manufacture of a pharmaceutical preparation for the treatment of anxiety disorders, depression, psychosis, impulse control disorders, alcohol abuse, ischaemic diseases, cardiovascular disorders, side effects induced by conventional antipsychotic agents and senile dementia.

The compounds of the invention have been found to displace tritiated 8-hydroxy-2-dipropylaminotetralin (8—OH—DPAT) from $5\text{-HT}_{1A}$ receptors in vitro, the majority of the compounds showing affinities higher than 50 nM. Furthermore, the present compounds have proven to cover a broad range of selectivities for $5\text{-HT}_{1A}$ receptors as compared to $\alpha_1$ adrenoceptors and $D_2$ receptors. Some of the compounds of the present invention are highly selective for the $5\text{-HT}_{1A}$ receptors, while other compounds of the present invention have affinities to some of the above mentioned binding sites. The present compounds have also been shown to cover a wide range of efficacies.

An especially interesting group of compounds show high affinity to both $5\text{-HT}_{1A}$ and $D_2$ receptors. In view of the fact that dopamine $D_2$ antagonists are effective in the treatment of schizophrenic disorders (see e.g. Lowe et al, *Med. Res. Rev.*, 1988, 8, 475) and since $5\text{-HT}_{1A}$ agonists, as mentioned above, can alleviate neuroleptica induced side effects, such compounds are useful in the treatment of schizophrenic disorders.

Accordingly, the compounds of the invention have proven to be useful for the treatment of anxiety disorders, depression, psychosis, impulse control disorders, alcohol abuse, ischaemic diseases, cardiovascular disorders, side effects induced by conventional antipsychotic agents and senile dementia.

DETAILED DESCRIPTION OF THE INVENTION

Some of the compounds of general Formula I may exist as optical isomers thereof to and such optical isomers are also embraced by the invention.

As used herein the term alkyl refers to a $C_1$–$C_{20}$ straight chain or branched alkyl group and similarly alkenyl and alkynyl mean a $C_2$–$C_{20}$ straight chain or branched hydrocarbon group having one or more double bonds or triple bonds, respectively. The term cycloalkyl designates a carbocyclic ring having 3–8 carbon atoms, inclusive, or a bicyclic or tricyclic carbocycle, such as adamantyl.

In the formulas included in the definition of X, the dotted lines indicate optional bonds, i.e. in case a dotted line represents a bond, the bond in question is a double bond. Of course double bonds may not be present in adjacent positions and the arrangement of the bonds may not be in conflict with the conventional rules as readily understood by a person skilled in the art.

The expression alk(en/yn)yl means that the group may be an alkyl, alkenyl or alkynyl group.

The terms lower alkyl, lower alkoxy, lower alkylthio, etc. designate such branched or unbranched groups having from one to six carbon atoms inclusive. Exemplary of such groups are methyl, ethyl, 1-propyl, 2-propyl, 1-butyl, 2-butyl, 2-methyl-2-propyl, 2-methyl-1-propyl, methoxy, ethoxy, 1-propoxy, methylthio, ethylthio, 1-propylthio, 2-propylthio, methylsulfonyl, ethylsulfonyl, or the like.

The term aryl is intended to mean a carbocyclic or heterocyclic aromatic monocyclic or fused bicyclic group or a biphenyl group. Examples of groups are: thienyl, furyl, oxazolyl, isoxazolyl, thiazolyl, isothiazolyl, pyrazolyl, imidazolyl, triazolyl, oxadiazolyl, thiadiazolyl, tetrazolyl, benzofuranyl, benzothienyl, benzisothiazolyl, benzisoxazolyl, indolyl, phenyl, pyridyl, pyrimidinyl, pyridazinyl, naphthyl, quinolinyl, and quinazolinyl, in particular phenyl, thienyl, naphtyl, or furanyl.

In Formula I, A is preferably a 2 to 6 membered alkylene group.

B is preferably SO, $SO_2$ or a group of Formula II, as defined above wherein W is O and Z is selected from —$(CH_2)_n$— n being 2 or 3, —CH=CH— or 1,2-phenylene optionally substituted with halogen or trifluoromethyl.

X is preferably selected from the group of divalent 3–4 membered groups consisting of

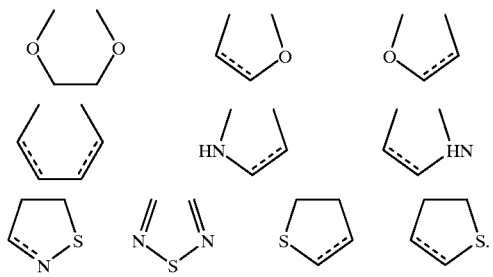

$R^1$ is preferably lower alkyl, aryl, cycloalkyl or aryl-lower alkyl, most preferably lower alkyl, phenyl, phenyl substituted with one of the substituents as defined above, $C_5$–$C_6$ cycloalkyl, adamantyl, phenyl-lower alkyl optionally substituted with one of the substituents as defined above or naphthyl.

$R^2$ and $R^3$ are preferably both hydrogen.

$R^4$, $R^5$, and $R^6$ are preferably independently selected from the group consisting of hydrogen and halogen.

$R^7$ and $R^8$ are preferably independently selected from the group consisting of hydrogen, lower alkyl, aryl, a group —$COOR^9R^9$ being hydrogen or lower alkyl and a group —$CONH_2$. Most preferably $R^7$ and $R^8$ are independently selected from hydrogen, lower alkyl, phenyl optionally substituted with one of the substituents as defined above, a group —$COOR^9R^9$ being hydrogen or lower alkyl and a group —$CONH_2$.

The acid addition salts of the invention are pharmaceutically acceptable salts of the compounds of Formula I formed with non-toxic acids. Exemplary of such organic salts are those with maleic, fumaric, benzoic, ascorbic, embonic, succinic, oxalic, bis-methylenesalicylic, methanesulfonic, ethanedisulfonic, acetic, propionic, tartaric, salicylic, citric, gluconic, lactic, malic, mandelic, cinnamic, citraconic, aspartic, stearic, palmitic, itaconic, glycolic, p-aminobenzoic, glutamic, benzenesulfonic, and theophylline acetic acids, as well as the 8-halotheophyllines, for example 8-bromotheophylline. Exemplary of such inorganic salts are those with hydrochloric, hydrobromic, sulfuric, sulfamic, phosphoric, and nitric acids.

The pharmaceutical compositions of this invention or those which are manufactured in accordance with this invention may be administered by any suitable route, for example orally in the form of tablets, capsules, powders, syrups, etc., or parenterally in the form of solutions for injection. For preparing such compositions methods well known in the art may be used, and any pharmaceutically acceptable carriers, diluents, exipients, or other additive usually used in the art may be used.

Conveniently, the compounds of the invention are administered in unit dosage form containing said compounds in an amount of about 0.01 to 50 mg. The total daily dose usually ranges of about 0.05–500 mg, and most preferably about 0.1 to 20 mg of the active compound of the invention.

The compounds of Formula I are prepared by:

a) reacting a compound of Formula III

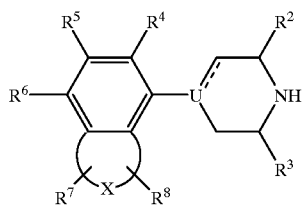

III wherein $R^2$–$R^8$, U, X, and the dotted line are as previously defined, with a reagent of the formula $R^1$—B—A—V wherein $R^1$, A, and B are as previously defined and V is a suitable leaving group such as halogen, mesylate or tosylate;

b) reducing the amide carbonyl of a compound of Formula IV

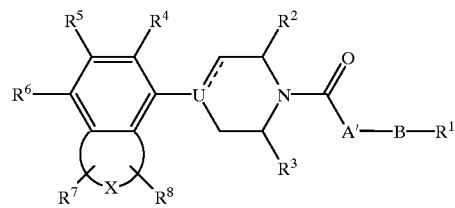

IV wherein $R^1$–$R^8$, B, U, X, and the dotted line are as previously defined and A' is such a group that $CH_2$—A' is a 2 to 6 membered branched or straight chain alkylene, alkenylene or alkynylene group which is optionally substituted with aryl or hydroxy as comprised by the definition of A;

c) reductive alkylation of an amine of Formula III as previously defined with an aldehyde of the formula $R^1$—B—A'—CHO, a carboxylic acid of the formula $R^1$—B—A'—COOH or a ketone of the formula $R^1$—B—A"—CO—A"' wherein $R^1$, B and A' are as previously defined and A" and A"' are such groups that A"—CH—A"' is a 2 to 6 membered branched or straight chain alkylene, alkenylene or alkynylene group optionally substituted with aryl or hydroxy as comprised by the definition of A;

d) oxidation of the sulfide sulfur atom in a compound of Formula V

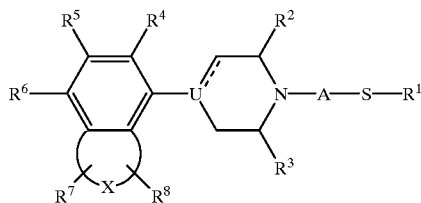

V wherein $R^1$–$R^8$, A, U, X, and the dotted line are as previously defined, to the corresponding sulfoxide or sulfone;

e) 1,4-addition of an amine of general Formula III as previously defined to a α,β-unsaturated compound of formula $R^{12}R^{13}C=CR^{14}$—B—$R^1$, wherein $R^1$ and B are as previously defined and $R^{12}$, $R^{13}$, and $R^{14}$ are such groups that $R^{12}R^{13}C=CR^{14}$ is a 2–6 membered branched or straight chain alkenylene group optionally substituted with aryl or hydroxy as comprised by the definition of A;

f) reductive alkylation of the NH group of a compound of general Formula VI

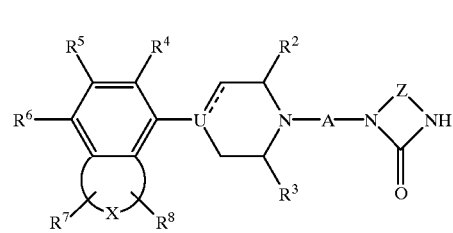

VI wherein $R^2$–$R^8$, A, U, X, Z, and the dotted line are as previously defined, with an aldehyde of the formula $R^{1'}$—CHO, a carboxylic acid of the formula $R^{1'}$—COOH or a ketone of the formula $R^{1''}$—CO—$R^{1'''}$ wherein $R^{1'}$, $R^{1''}$, and $R^{1'''}$ are such groups that $R^{1'}$—$CH_2$ and $R^{1''}$—$CH_2$-$R^{1'''}$, respectively, are groups comprised by the above definition of $R^1$;

g) cyclization of a compounds of general Formula VII

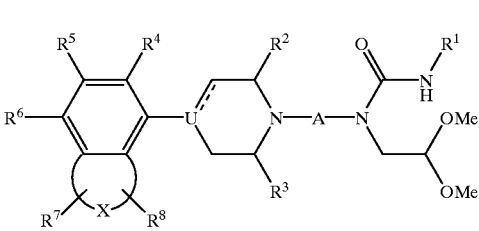

VII wherein $R^1$–$R^8$, A, U, X, and the dotted line are as previously defined;

h) arylation of the NH group of a compound of general Formula VIII

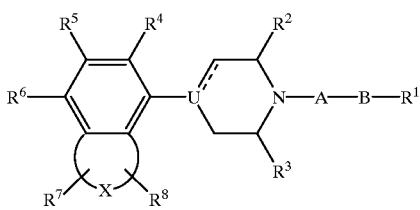

VIII wherein A, B, $R^1$—$R^8$, the dotted line and U is as previously defined and X' is defined as X with the proviso that X' designates a heteroaromatic ring system containing a NH functionality, with an arylating agent of the formula Ar-hal wherein Ar is aryl as previously defined and hal is halogen;

i) transformation of a compound of general Formula I wherein $R^7$ or $R^8$ designates a group —$COOR^9$ to the corresponding compound wherein $R^7$ or $R^8$ designates a group —$CONR^{10}R^{11}$ in which formulas $R^7$–$R^{11}$ is as previously defined;

j) treating a compound of general Formula I in which the ring system defined by X comprises one or more double bonds in order to reduce one or more of said double bonds thereby obtaining a corresponding partially or completely reduced ring system;

k) reductive removal of one or more of the substituents $R^4$–$R^8$ in a compound of general Formula I in which one or more of these substituents are selected from the group consisting of chloro, bromo, or iodo;

l) reducing the double bond in the tetrahydropyridine ring of a compound of general Formula I in which U is C and the dotted line represents a bond in order to obtain the corresponding piperidine derivative;

whereupon the compound of Formula I is isolated as the free base or a pharmaceutically acceptable acid addition salt thereof.

The reaction of the compound of Formula III according to method a) is conveniently performed in an inert organic solvent such as a suitably boiling alcohol or ketone, preferably in the presence of a base (potassium carbonate or triethylamine) at reflux temperature.

The reagents of formula $R^1$—B—A—V wherein B is SO or $SO_2$ are obtained by oxidation of the corresponding sulfides according to methods well known in the art. The starting sulfides are prepared by standard literature methods.

Such reagents in which B represents a group of Formula II wherein Z is —$(CH_2)_2$— and W is O are prepared by the method disclosed in DE-OS No 2,035,370. Preparation of such reagents wherein Z is —CH═CH— or 1,2-phenylene is described in EXAMPLES 5 and 12–13, respectively.

Arylpiperazine derivatives of Formula III are conveniently prepared from the corresponding arylamines according to the method described by Martin et al, *J. Med. Chem.*, 1989, 32, 1052, or the method described by Kruse et al, *Rec. Trav. Chim Pays-Bas*, 1988, 107, 303.

The starting arylamines are either commercially available or are described in the literature as follows:

The synthesis of 5-amino-1,4-benzodioxane is described by Dauksas et al, *Zh. Org. Khim.*, 1967, 3, 1121.

The synthesis of 7-amino-2,3-dihydrobenzofuran is described in U.S. patent application Ser. No. 4,302,592.

The synthesis of ethyl 7-amino-2-indolyl carboxylate is described by Scriven et al, *J. Chem. Soc., Perkin Trans. I*, 1979, 53.

The synthesis of 7-aminobenzofuran is described by Van Wijngaarden et al, *J. Med. Chem.*, 1988, 31, 1934.

The synthesis of 7-amino-2,3-dihydro-2,2-dimethylbenzofuran is described in Ger. Offen. DE 3526510.

The synthesis of 7-amino-benzo[b]thiophene is described by Boswell et al, *J. Heterocycl. Chem.* 1968, 5, 69.

The synthesis of 7-aminoindole is described in U.S. patent application Ser. No. 4,506,078.

The synthesis of 7-amino-1,2-benzisothiazole is described by Ricci et al, *Ann. Chim. (Rome)*, 1963, 53, 1860.

The synthesis of 4-aminoindole is described by Melhado et al, *J. Org. Chem.*, 1983, 48, 5130.

4-Aminobenzofuran and ethyl 4-amino-2-benzofuranyl carboxylate are obtained by conventional reduction of the corresponding nitro compounds (Andrisano et al, *Gazz. Chim. Ital.*, 1956, 86, 1257).

7-Amino-2-phenylbenzofuran is obtained from 2-phenyl-7-benzofuranyl carboxylic acid (Eur. Pat. Appl. No. EP 147044 A2) via the Curtius rearrangement. Substituted derivatives of various ring systems are obtained by analogy methods to the above mentioned methods.

Piperidine and 1,2,5,6-tetrahydropyridine derivatives of Formula III are prepared by known methods, cf. e.g. U.S. Pat. No. 2,891,066; McElvain et al, *J. Amer. Chem. Soc.* 1950, 72, 3134, or are prepared as described in EXAMPLES 10 and 11.

The reduction according to method b) is preferably carried out in an inert organic solvent such as diethyl ether or tetrahydrofuran in the presence of lithium aluminium hydride at reflux temperature.

The amides of Formula IV are conveniently prepared by treating compounds of general Formula III with suitable carboxylic acid chlorides of formula $R^1$—B—A'—COCl in the presence of base (potassium carbonate or triethylamine). The carboxylic acid chlorides are prepared according to standard methods.

The reductive alkylation of the amines of Formula III according to method c) is performed by standard literature methods (see EXAMPLE 4). The aldehydes, carboxylic acids, and ketones of formulas $R^1$–B—A'—CHO, $R^1$—B—A'—COOH, and $R^1$—B—A"—CO—A''', respectively, are prepared according to standard methods.

The oxidation of sulfur according to method d) is performed by applying a well known oxidation agent, for example m-chloroperbenzoic acid, hydrogen peroxide, or potassium peroxymonosulfate. Sulfoxides are preferably prepared using m-chloroperbenzoic acid according to standard methods. Sulfones are preferably prepared using hydrogen peroxide in glacial acetic acid according to standard methods.

Sulfides of Formula V are prepared either by method a) using reagents of formula $R^1$—S—A—V, or by method b) using compounds of Formula IV where B is defined as S, or by method c) using aldehydes of formula $R^1$—S—A'—CHO or carboxylic acids of formula $R^1$—S—A'—COOH or ketones of formula $R^1$—S—A"—CO—A'''. All sulfide reagents mentioned are prepared according to standard methods.

The addition of amines to α,β-unsaturated compounds according to method e) is conveniently performed in an inert solvent such as methylene chloride at room temperature. Unsaturated compounds of formula $R^{12}R^{13}C$═$CR^{14}$—B—R are prepared by standard methods.

The reductive alkylation according to method f) is performed in glacial acetic acid using sodium borohydride as reducing agent. The starting compounds of Formula VI are prepared by methods analogous to methods a), b), and c).

The cyclization according to method g) is performed in ethanol in the presence of hydrochloric acid. The starting compounds of general Formula VII are prepared by alkylating amines of Formula III with chloroacetonitrile followed by alane reduction of the cyano group to the corresponding primary amine. Monoalkylation with 2-bromoacetaldehyde dimethyl acetal and subsequent addition of isocyanates give VII.

The arylation according to method h) is most conveniently performed by applying the well known Ullmann reacton. The arylating reagents, Ar-hal, are commercially available and the transformation of esters according to method i) is well-described in the literature.

The reduction of double bonds according to method j) is conveniently performed by catalytic hydrogenation in an alcohol with a platinum catalyst or by treatment with sodium cyanoborohydride in trifluoroacetic acid (see EXAMPLE 9) or by hydrogenation with diborane or a diborane precursor such as trimethylamine or dimethyl sulfide complex in tetrahydrofuran or dioxan from 0° C. to reflux temperature followed by acid catalyzed hydrolysis of the intermediate borane derivative.

The removal of halogen substituents according to method k) and reduction of the double bond according to method I) are conveniently performed by catalytic hydrogenation in an alcohol in the presence of a palladium catalyst or by treatment with ammonium formate in an alcohol at elevated temperatures in the presence of a palladium catalyst.

Whereupon the compound of Formula I is isolated as the free base or a pharmaceutically acceptable acid addition salt thereof.

EXAMPLES

In the following the invention is further illustrated by examples which, however, may not be construed as limiting.

Example 1

1-(1,4—Benzodioxan-5-yl)-4-(3-cyclohexylsulfonyl-1-propyl)piperazine, oxalate, 1a To a suspension of potassium tert-butoxide (100 g) in toluene (600 ml) cyclohexylthiol (100 g) was added dropwise. After stirring for half an hour at room temperature 3-bromo-1-propanol (100 g) was added dropwise. The mixture was stirred at 60° C. for 3 hours. The mixture was poured into 2 M sodium hydroxide solution (1 l). The phases were separated and the organic phase washed with 2 M sodium hydroxide (500 ml). Removal of solvent in vacuo left a colorless oil (120 g) of 3-cyclohexylthio-1-propanol which was sufficiently pure for use in the next step.

To a solution of 3-cyclohexylthio-1-propanol (60 g) in glacial acetic acid (250 ml) hydrogen peroxide (35% in water, 210 ml) was added at 10° C. followed by reflux for 2 h. After cooling the mixture was poured onto ice followed by extraction with ethyl acetate (1 l). The organic phase was washed several times with 1 M sodium hydroxide. Removal of solvent gave an oil which was treated at reflux temperature with 1 M sodium hydroxide (600 ml) for 1 h. Extraction with ethyl acetate, drying of the organic phase over magnesium sulfate, and removal of solvent in vacuo gave a colorless oil (37 g) of 3-cyclohexylsulfonyl-1-propanol which was used without further purification in the next step.

A solution of 3-cyclohexylsulfonyl-1-propanol (37 g) and triethylamine (30 ml) in methylene chloride (400 ml) was treated dropwise at −5° C. with methanesulfonyl chloride (15 ml). After stirring for 2 h at room temperature the mixture was washed with water and dried over magnesium sulfate. Removal of solvent in vacuo gave a viscous oil (49 g) of 3-cyclohexylsulfonyl-1-propyl methanesulfonate.

A mixture of 3-cyclohexylsulfonyl-1-propyl methanesulfonate (8.5 g), 1-(1,4-benzodioxan-5-yl)-piperazine (5.4 g), and potassium carbonate in methyl isobutyl ketone (200 ml) was refluxed for 20 h. Filtration and removal of solvent in vacuo gave an oil which was purified by column chromatography (silica gel, eluent: ether/methanol/triethylamine=96:2:2). The title compound crystallized as the oxalate salt from acetone by addition of oxalic acid. Yield: 8.1 g, mp: 162–64° C.
$^1$H NMR ($\delta$, DMSO): 1.05–1.45 (m, 6H), 1.60–1.90 (m, 2H), 1.95–2.10 (m, 4H), 2.90–3.20 (m, 13 H), 4.15–4.30 (m, 4H), 6.45–6.60 (m, 2H), 6.75 (d, 1H).

In a similar manner were also prepared:

1-(1,4—Benzodioxan-5-yl)-4-(3-phenylsulfonyl-1-propyl)piperazine, hydrochloride, 1b, mp: 184–96° C. $^1$H NMR ($\delta$, DMSO): 2.00–2.20 (m, 2H), 3.00–3.25 (m, 6H), 3.30–3.60 (m, 6H), 4.15–4.30 (m, 4H), 6.45–6.60 (m, 2H), 6.75 (t, 1H), 7.60–7.80 (m, 3H), 7.95 (d, 2H), 8.00 (b, 2H).

1-(3—Cyclohexylsulfonyl-1-propyl)-4-(2,3-dihydrobenzofuran-7-yl)piperazine, maleate, 1c, mp: 166–68° C. $^1$H NMR ($\delta$, DMSO): 1.05–1.50 (m, 5H), 1.60–1.70 (m, 1H), 1.75–1.90 (m, 2H), 1.95–2.20 (m, 4H), 3.00–3.40 (m, 17H), 4.50 (t, 2H), 6.05 (s, 2H), 6.65–6.80 (m, 2H), 6.90 (d, 1H).

1-(2,3—Dihydrobenzofuran-7-yl)-4-(3-methylsulfonyl-1-propyl)piperazine, maleate, 1d, mp: 150–51° C. $^1$H NMR ($\delta$, DMSO): 2.00–2.20 (m, 2H), 3.05 (s, 3H), 3.00–3.50 (m, 16H), 4.55 (t, 3H), 6.10 (s, 2H), 6.65–6.85 (m, 2H), 6.90 (d, 1H).

1-(1-4—Benzodioxan-5-yl)-4-(3-isopropylsulfonyl-1-propyl)piperazine, fumarate, 1e, mp: 166–67° C. $^1$H NMR ($\delta$, DMSO): 1.25 (d, 6H), 1.80–2.00 (m, 2H), 2.50–2.65 (m, 6H), 2.90–3.05 (m, 4H), 3.05–3.15 (m, 2H), 3.30 (h, 1H), 4.15–4.30 (m, 4H), 6.50 (t, 2H), 6.60 (s, 2H), 6.70 (t, 1H).

1-[3-(1—Adamantyl)sulfonyl-1-propyl]-4-(1,4-benzodioxan-5-yl)piperazine, 1f, mp: 143–44° C. $^1$H NMR ($\delta$, CDCL$_3$): 1.65–1.85 (m, 6H), 2.00–2.25 (m, 11H), 2.55 (t, 2H), 2.60–2.70 (m, 4H), 2.90–3.00 (m, 2H), 3.00–3.15 (m, 4H), 4.20–4.25 (m, 2H), 4.25–4.35 (m, 2H), 6.50–6.60 (m, 2H), 6.80 (t, 1H).

Example 2

1-[3-[4-(1,4—Benzodioxan-5-yl)-1-piperazinyl]-1-propyl]-3-phenyl-2-imidazolidinone, hydrochloride, 2a.

A mixture of 1-(1,4-benzodioxan-5-yl)-piperazine (1.5 g), 1-(3-chloro-1-propyl)-3-phenyl-2-imidazolidinone (1.4 g), potassium carbonate (3 g), and potassium iodide (0.1 g) in methyl isobutyl ketone was refluxed for 20 h. Filtration and removal of solvent in vacuo gave a viscous oil which was separated by column chromatography (silica gel, eluent: ethyl acetate/methanol/triethylamine=15:4:1). The title compound was isolated as an oil which crystallized as the hydrochloride salt from acetone by addition of hydrochloric acid. Yield: 1.9 g, mp: 229–32° C. $^1$H NMR ($\delta$, DMSO): 1.95–2.15 (m, 2H), 3.00–3.25 (m, 6H), 3.30 (t, 2H), 3.40–3.65 (m, 4H), 3.70–4.00 (m, 4H), 4.15–4.30 (m, 4H), 6.45–6.70 (m, 2H), 6.75 (t, 1H), 7.00 (t, 1H), 7.30 (t, 2H), 7.60 (d, 2H), 11.30 (b, 1H).

In a similar manner were also prepared:

1-[2-[4-(1,4—Benzodioxan-5-yl)-1-piperazinyl]ethyl]-3-cyclopentyl-2-imidazolidinone, hydrochloride, 2b, mp: 266–68° C. $^1$H NMR ($\delta$, CDCl$_3$): 1.45–1.95 (m, 8H), 3.00–3.30 (m, 4H), 3.35–3.60 (m, 8H), 3.60–3.85 (m, 4H), 4.15–4.35 (m, 5H), 6.50 (d, 1H), 6.65 (d, 1H), 6.80 (t, 1H), 12.30 (b, 1H).

1-[2-[4-(1,4—Benzodioxan-5-yl )-1-piperazinyl]ethyl]-3-phenyl-2-imidazolidinone, hydrochloride, 2c, mp: 288–90° C. $^1$H NMR ($\delta$, DMSO): 3.00–3.75 (m, 10H), 3.85 (t, 2H), 4.10–4.35 (m, 4H), 4.50–4.75 (m, 4H), 6.45–6.70 (m, 2H), 6.75 (t, 1H), 7.00 (t, 1H), 7.35 (t, 2H), 7.60 (d, 2H).10.95 (b, 1H).

1-[2-[4-(1,4—Benzodioxan-5-yl)-1-piperazinyl]ethyl]-3-cyclohexyl-2-imidazolidinone, fumarate, 2d, mp: 103–14° C. ¹H NMR (δ, DMSO): 0.95–1.15 (m, 1H), 1.15–1.45 (m, 4H), 1.45–1.65 (m, 3H), 1.65–1.80 (m, 2H), 2.60 (t, 2H), 2.65–2.80 (m, 4H), 2.90–3.05 (m, 4H), 3.15–3.35 (m, 6H), 3.40–3.55 (m, 1H), 4.15–4.30 (m, 4H), 6.4–6.55 (m, 2H), 6.60 (s, 2H), 6.70 (t, 1H), 7.90 (b, 1H).

1-[4-[4-(1,4—Benzodioxan-5-yl)-1-piperazinyl]-1-butyl]-3-cyclohexyl-2-imidazolidinone, hydrochloride, 2e, mp: 212–221° C. ¹H NMR (δ, DMSO): 0.95–1.15 (m, 1H), 1.15–1.40 (m, 4H), 1.40–1.65 (m, 5H), 1.65–1.85 (m, 4H), 3.00–3.25 (m, 8H), 3.25 (2, 4H), 3.40–3.60 (m, 5H), 4.15–4.30 (m, 4H), 6.45–6.60 (m, 2H), 6.75 (t, 1H), 8.00 (b, 1H), 11.40 (b, ₁H).

1—Cyclopentyl-3-[2-[4-(2,3-dihydrobenzofuran-7-yl)-1-piperazinyl]ethyl]-2-imidazolidinone, hydrochloride, 2f, mp: 200–2° C. ¹H NMR (δ, DMSO): 1.40–1.80 (m, 8H), 3.00–3.80 (m, 18H), 4.00–4.15 (m, 1H), 4.50 (t, 2H), 6.65–6.85 (m, 2H), 6.90 (t, 1H), 11.05 (b, 1H).

1-[3-[4-(2,3—Dihydrobenzofuran-7-yl)-1-piperazinyl]-1-propyl]-3-phenyl-2-imidazolidinone, hydrochloride, 2g, mp: 225–28° C. ¹H NMR (δ, DMSO): 1.95–2.10 (m, 2H), 2.95–3.40 (m, 12H), 3.40–3.70 (m, 6H), 3.80 (t, 2H), 4.50 (t, 2H), 6.65–6.80(m, 2H), 6.90 (d, 1H), 7.00 (t, 1H), 7.35 (t, 2H), 7.60 (d, 2H), 11.20 (b, 1H).

4-[4-[2-(3—Phenylimidazolidin-2-on-1-yl)ethyl]-1-piperazinyl]-2,1,3-benzothiadiazole, maleate, 2h, mp: 182–83° C. ¹H NMR (δ, DMSO): 3.20–3.95 (m, 18H), 6.10 (s, 2H), 6.90–7.10 (m, 2H), 7.35 (t, 2H), 7.55–7.70 (m, 4H).

1-[2-[4-(2,3—Dihydrobenzofuran-7-yl)-1-piperazinyl]ethyl]-3-(4-fluorophenyl)-2-imidazolidinone, fumarate, 2i, mp: 188–90° C. ¹H NMR (δ, DMSO): 2.55–2.70 (m, 6H), 2.95–3.15 (m, 4H), 3.10 (t, 2H), 3.35 (t, 2H), 3.55 (t, 2H), 3.80 (t, 2H), 4.50 (t, 2H), 5.10 (b, 2H), 6.60 (s, 2H), 6.65 (d, 1H), 6.75 (t, 1H), 6.80 (d, 1H), 7.15 (t, 2H), 7.50–7.60 (m, 2H).

Ethyl 7-[4-[2-(3-phenyl-2-imidazolidin-2-on-1-yl)ethyl]-1-piperazinyl]-2-indolyl carboxylate, fumarate, 2j, mp: 202–4° C. ¹H NMR (δ, DMSO): 1.35 (t, 3H), 2.70 (t, 2H), 2.75–2.90 (m, 4H), 2.95–3.15 (m, 4H), 3.40 (t, 2H), 3.60 (t, 2H), 3.80 (t, 2H), 4.35 (q, 2H), 6.60 (s, 2H), 6.80 (d, 1H), 6.95–7.05 (m, 2H), 7.15 (d, 1H), 7.25–7.40 (m, 2H), 7.60 (d, 2H).

1-[2-[4-(1—Naphtyl)-1-piperazinyl]ethyl]-3-phenyl-2-imidazolidinone, fumarate, 2k, mp: 176–80° C. ¹H NMR (δ, DMSO): 2.70 (t, 2H), 2.65–2.90 (m, 4H), 2.95–3.15 (m, 4H), 3.40 (t, 2H), 3.55 (t, 2H), 3.80 (t, 2H), 6.60 (s, 2H), 7.00 (t, 1H), 7.10 (d, 1H), 7.30 (t, 2H), 7.40 (t, 1H), 7.45–7.65 (m, 5H), 7.85–7.95 (m, 1H), 8.05–8.20 (m, 1H).

1-[2-[4-(1,4—Benzodioxan-5-yl)-1-piperazinylethyl]-3-ethyl]-2-imidazolidinone, hydrochloride, 2l, mp: 250–52° C. ¹H NMR (δ, DMSO): 1.05 (t, 3H), 2.95–3.70 (m, 18H), 4.15–4.30 (m, 4H), 6.50 (d, 1H), 6.55 (d, 1H), 6.25 (t, 1H), 10.65 (b, 1H).

1-[2-[4—Benzofuran-7-yl-1-piperazinyl)ethyl]-3-phenyl-2-imidazolidinone, hemifumarate, 2m, mp: 175–76° C. ¹H NMR (δ, DMSO): 2.60 (t, 2H), 2.65–2.75 (m, 4H), 3.20–3.35 (m, 4H), 3.40 (t, 2H), 3–60 (t, 2H), 3.80 (t, 2H), 6.75 (s, 1H), 6.75 (d, 1H), 6.90 (s, 1H), 7.00 (t, 1H), 7.05–7.25 (m, 2H), 7.30 (t, 1H), 7.60 (d, 1H), 7.95 (s, 1H).

1-[2-[4-(2,3-dimethyl-2,2-dimethylbenzofuran-7-yl)-1-piperazinyl]ethyl]-3-phenyl-2-imidazolidinone, dihydrochloride, 2n, mp: 220–30° C. ¹H NMR (δ, DMSO): 1.40 (s, 6H), 3.00 (s, 2H), 3.10–3.45 (m, 6H), 3.50–3.75 (m, 8H), 3.85 (t, 2H), 6.65–6.80 (m, 2H), 6.85 (d, 1H), 7.00 (t, 1H), 7.35 (t, 2H), 7.60 (d, 2H), 9.35 (b, 1H), 11.30 (b, 1H).

1-[2-[4-(1,4—Benzodioxan-5-yl)-1-piperazinyl]ethyl]-3-isopropyl-2-imidazolidinone, hydrochloride, 2o, mp: 228–30° C. ¹H NMR (δ, DMSO): 1.05 (d, 6H), 2.95–3.65 (m, 16H), 3.90 (h, 1H), 4.15–4.30 (m, 4H), 6.50 (d, 1H), 6.60 (d, 1H), 6.25 (d, 1H), 10.95 (b, 1H).

1—Cyclopentyl-3-[2-[4-(2,3-dihydro-2,2-dimethylbenzofuran-7-yl)-1-piperazinyl]ethyl]-2-imidazolidinone, dihydrochloride, 2p, mp: 185–95° C. ¹H NMR (δ, DMSO): 1.45 (s, 6H), 1.45–1.75 (m, 8H), 3.00 (s, 2H), 3.10–3.40 (m, 10H), 3.50 (t, 2H), 3.55–3.70 (m, 4H), 4.00–4.15 (m, 1H), 6.70–6.80 (m, 2H), 6.35 (d, 1H), 7.35 (b, 1H), 11.30 (b, 1H).

1—Adamantyl-3-[2-[4-(1,4-benzodioxan-5-yl)-1-piperazinyl]ethyl]-2-imidazolidinone, hydrochloride, 2q, mp: 246–48° C. ¹H NMR (δ, DMSO): 1.55–1.65 (m, 6H), 1.90–2.10 (m, 9H), 2.96–3.60 (m, 16H), 4.15–4.30 (m, 4H), 6.50 (d, 1H), 6.55 (d, 1H), 6.75 (t, 1H), 10.85 (b, 1H).

1-[2-(4—Benzofuran-4-yl-1-piperazinyl)ethyl]-3-phenyl-2-imidazolidinone, sesquifumarate, 2r, mp: 207–9° C. ¹H NMR (δ, DMSO): 2.65 (t, 2H), 2.70–2.80 (m, 4H), 3.10–3.20 (m, 4H), 3.40 (t, 2H), 3.55 (t, 2H), 3.80 (t, 2H), 6.60 (s, 3H), 6.65–6.70 (m, 1H), 6.95–7.05 (m, 2H), 7.10–7, 20 (m, 2H), 7.30 (t, 2H), 7.55 (d, 2H), 7.90 (s, 1H).

1-[2-(4—Benzofuran-4-yl-1-piperazinyl)ethyl]-3-cyclopentyl-2-imidazolidinone, dihydrochloride, 2s, mp: 237–39° C. ¹H NMR (δ, DMSO): 1.40–1.80 (m, 8H), 3.15–3.45 (m, 10H), 3.55 (t, 2H), 3.55–3.75 (m, 4H), 4.00–4.20 (m, 1H), 4.45 (b, 1H), 6.75 (dd, 1H), 7.10 (d, 1H), 7.20–7.30 (m, 2H), 8.00 (s, 1H), 11.20 (b, 1H).

1-[2-(4—Benzo[b]thiophen-7-yl-1-piperazinyl)ethyl]-3-phenyl-2-imidazolidinone, 2t, mp: 136–38° C. ¹H NMR (δ, CDCl₃): 2.70 (t, 2H), 2.70–2.85(m, 4H), 3.15–3.35 (m, 4H), 3.50 (t, 2H), 3.55 (t, 2H), 3.80j (t, 2H), 6.90 (d, 1H), 7.00 (t, 1H), 7.20–7.45 (m, 5H), 7.45–7.65 (m, 3H).

1—Cyclopentyl-3-[2-[4-(7-indolyl)-1-piperazinyl]ethyl]-2-imidazolidinone, 2u, mp: 188–89° C. ¹H NMR (δ, CDCl₃): 1.40–1.90 (m, 8H), 2.60 (t, 2H), 2.65–2.75 (m, 4H), 3.05–3.15 (m, 4H), 3.20–3.45 (m, 6H), 4.25 (p, 1H), 6.50–6.55 (m, 1H), 6.80 (d, 1H), 7.05 (t, 1H), 7.10–7.20 (m, 1H), 7.35 (d, 1H), 8.40 (b, 1H).

1-[2-[4-(7—Indolyl)-1-piperazinyl]ethyl]-3-phenyl-2-imidazolidinone, fumarate, 2v, mp: 215–16° C. ¹H NMR (δ, DMSO): 2.70 (t, 2H), 2.75–2.85 (m, 4H), 3.00–3.15 (m, 4H), 3.40 (t, 2H), 3.55 (t, 2H), 3.80 (t, 2H), 6.35–6.40 (m, 1H), 6.60 (s, 2H), 6.65 (d, 1H), 6.90 (t, 1H), 7.00 (t, 1H), 7.15–7.35 (m, 4H), 7.60 (d, 2H).

1-[2-[4-(1,2—Benzisothiazol-7-yl)-1-piperazinyl]ethyl]-3-phenyl-2-imidazolidinone, hydrochloride, 2x, mp: 237–44° C. ¹H NMR (δ, DMSO): 3.10–3.80 (m, 14H), 3.85 (t, 2H), 7.00 (t, 1H), 7.20 (d, 1H), 7.30 (t, 2H), 7.50 (t, 1H), 7.60 (d, 2H), 7.90 (d, 1H), 9.15 (s, 1H), 11.25 (b, 1H).

1—Cyclopentyl-3-[2-[4-(4-indolyl)-1-piperazinyl]ethyl]-2-imidazolidinone-dihydrochloride, 2y, mp: 214–20° C. ¹H NMR (δ, DMSO): 1.50–1.80 (m, 8H), 3.20–3.60 (m, 12H), 3.60–3.80 (m, 4H), 3.95–4.20 (m, 1H), 6.60j (s, 1H), 6.70 (d, 1H), 7,00 (t, 1H), 7.20 (d, 1H), 7.35 (s, 1H), 11.30 (b, 1H).

1-[2-[4-(4—Indolyl)-1-piperazinyl]ethyl]-3-phenyl-2-imidazolidinone, dihydrochloride, 2z, mp: 233–38° C. ¹H NMR (δ, DMSO): 3.25–3.50 (m, 8H), 3.60 (t, 2H), 3.60–3.75 (m, 4H), 3.85 (t, 2H), 5.00 (b, 2H), 6.50 (2, 1H), 6.60 (d, 1H), 6.95–7.00 (m, 2H), 7.15 (d, 1H), 7.25–7.40 (m, 3H), 7.60 (d, 2H), 11.20 (b, 1H).

1-[2-[4—Benzo[b]thiophen-7-yl-1-piperazinyl]ethyl]-3-cyclopentyl-2-imidazolidinone, hydrochloride, 2aa, mp: 264–67° C. ¹H NMR (δ, DMSO): 1.40–1.75 (m, 8H), 3.20–3.45 (m, 10H), 3.50 (t, 2H), 3.60–3.75 (m, 4H), 4.10 (p, 1H), 7.05 (d, 1H), 7.40 (t, 1H), 7.50 (d, 1H) 7.60 (d, 1H), 7.75 (d, 1H), 11.30 (b, 1H).

1—Cyclohexyl-3-[4-[4-(2,3-dihydro-2,2-dimethylbenzofuran-7-yl)-1-piperazinyl]-1-butyl]-2- imidazolidinone, dihydrochloride, 2bb, mp: 196–203° C. $^1$H NMR (δ, DMSO): 1.20–1.65 (m, 10H), 1.40 (s, 6H), 1.65–1.80 (m, 4H), 3.00 (s, 2H), 3.00–3.20 (m, 8H), 3.20–3.25 (m, 6H), 3.40–3.55 (m, 2H), 3.60–3.65 (m, 1H), 6.70–6.80 (m, 2H), 6.85 (d, 1H), 7.60 (b, 1H), 11.30 (b, 1H).

Ethyl [4-[4-[2-(3-cyclopentyl-2-imidazolidinon-1-yl)ethyl]-1-piperazinyl]-2-benzofuranyl]carboxylate, hydrochloride 2cc, mp: 198–201° C. $^1$H NMR (δ, DMSO): 1.35 (t, 3H), 1.40–1.75 (m, 8H), 3.25–3.75 (m, 16H), 4.00–4.15 (m, 1H), 4.35 (q, 2H), 6.80 (d, 1H), 7.30 (d, 1H), 7.40 (t, 1H), 7.95 (s, 1H).

1-[4-[4-(2,3—Dihydro-2,2-dimethylbenzofuran-7-yl)-1-piperazinyl]-1-butyl]-3-(4-fluorophenyl)-2-imidazolidinone, 2dd, mp: 158–60° C. $^1$H NMR (δ, CDCl$_3$): 1.50 (s, 6H), 1.55–1.65 (m, 4H), 2.45 (t, 2H), 2.55–2.70 (m, 4H), 3.00 (s, 2H), 3.10–3.20 (m, 4H), 3.30 (t, 2H), 3.45 (t, 2H), 3.80 (t, 2H), 6.65–6.70 (m, 1H), 6.75 (d, 2H), 7.00 (t, 2H), 7.40–7.55 (m, 2H).

1-[2-[4-(1,4—Benzodioxan-5-yl)-1-piperazinyl]ethyl]-3-t-butyl-2-imidazolidinone, hydrochloride, 2ee, mp: 229–31° C. $^1$H NMR (δ, DMSO): 1.30 (s, 9H), 3.00–3.60 (m, 16H), 4.20–4.30 (m, 4H), 6.45–6.60 (m, 2H), 6.75 (t, 1H).

1-[3-[4-(2,3—Dihydro-2,2-dimethylbenzofuran-7-yl)-1-piperazinyl]-1-propyl]-3-phenyl-2-imidazolidinone, fumarate, 2ff, mp: 183–85° C. $^1$H NMR (δ, DMSO): 1.40 (s, 6H), 1.75 (hep, 2H), 2.50 (t, 2H), 2.60–2.70 (m, 4H), 2.95 (s, 2H), 3.00–3.15 (m, 4H), 3.25 (t, 2H), 3.45 (t, 2H), 3.80 (t, 2H), 6.60 (s, 2H), 6.65 (d, 1H), 6.70 (t, 1H), 6.75 (d, 1H), 7.00 (t, 1H), 7.30 (t, 2H), 7.55 (d, 2H).

1—Adamantyl-3-[4-[4-(2,3-dihydro-2,2-dimethylbenzofuran-7-yl)-1-piperazinyl]-1-butyl]-2-imidazolidinone, 2gg, mp: 125–27° C. $^1$H NMR (δ, CDCl$_3$): 1.50 (s, 6H), 1.50–1.55 (m, 3H), 1.65–1.70 (m, 6H), 2.00–2.10 (m, 9H), 2.40 (t, 2H), 2.55–2.65 (m, 4H), 3.00 (s, 2H), 3.10–3.20 (m, 8H), 3.30 (t, 2H), 6.70 (t, 1H), 6.75 (d, 2H).

1-[4-[4-(5—Chloro-2-phenylbenzofuran-7-yl)-1-piperazinyl]-1-butyl]-3-cyclohexyl-2-imidazolidinone, dihydrochloride, 2hh,-mp: 198–200° C. $^1$H NMR (δ, DMSO): 1.00–1.85 (m, 14H), 3.10 (t, 2H), 3.15–3.70 (m, 14H), 4.00–4.10 (m, 1H), 4.65 (b, 2H), 6.85 (s, 1H), 7.30 (s, 1H), 7.40 (s, 1H), 7.45 (t, 1H), 7.50 (t, 2H), 7.95 (d, 2H).

1-[2-[4-(5—Chloro-2-phenylbenzofuran-7-yl)-1-piperazinyl]ethyl]-3-cyclopentyl-2-imidazolidinone, fumarate, 2ii, mp: 155–57° C. $^1$H NMR (δ, DMSO): 1.40–1.70 (m, 8H), 2.55 (t, 2H), 2.65–2.75 (m, 4H), 3.20–3.45 (m, 10H), 4.00–4.15 (m, 1H), 6.60 (s, 2H), 6.70 (s, 1H), 7.20 (s, 1H), 7.35(s, 1H), 7.45 (t, 1H), 7.50 (t, 2H), 7.90 (d, 2H).

1-[4-[4-(2,3—Dihydro-2,2-dimethylbenzofuran-7-yl)-1-piperazinyl]-1-butyl]-3-(1-naphtyl)-2-imidazolidinone, fumarate, 2jj, mp: 220–21° C. $^1$H NMR (δ, DMSO): 1.40 (s, 6H), 1.50–1.65 (m, 4H), 2.55 (t, 2H), 2.65–2.75 (m, 4H), 2.95 (s, 2H), 3.05–3.15 (m, 4H), 3.25 (t, 2H), 3.60 (t, 2H), 3.80 (t, 2H), 6.60 (s, 2H), 6.65 (d, 1H), 6.70 (t, 1H), 6–80 (d, 1H), 7.45 (d, 1H), 7.45–7.60 (m, 3H), 7.85–8.00 (m, 3H).

1—Cyclohexyl-3-[3-[4-(2,3-dihydro-2,2-dimethylbenzofuran-7-yl)-1-piperazinyl]-1-propyl]-2-imidazolidinone,oxalate, 2kk, mp: 191–92° C. $^1$H NMR (δ, DMSO): 1.00–1.90 (m, 1H), 1.40 (s, 6H), 2.90–3.00 (m, 4H), 3.10 (t, 2H), 3.15–3.30 (m, 10H), 3.40–3.50 (m, 1H), 4.10 (b, 2H), 6.65 (d, 1H), 6.70 (t, 1H), 6.80 (d, 1H).

1-[4-[4-(2,3—Dihydro-2,2-dimethyl-5-fluorobenzofuran-7-yl)-1-piperazinyl]-1-butyl]-3-(4-fluorophenyl)-2-imidazolidinone,oxalate, 2ll, mp: 126–27° C. $^1$H NMR (δ, DMSO): 1.45 (s, 6H), 1.50–1.65 (m, 4H), 2.40 (t, 2H), 2.55–2.65 (m, 4H), 2.95 (s, 2H), 3.05–3.20 (m, 4H), 3.30 (t, 2H), 3.95 (t, 2H), 3.80 (t, 2H), 6.30–6.50 (m, 2H), 7.00 (t, 2H), 7.40–7.55 (m, 2H).

1—Cyclohexyl-3-[4-[4-(2,3dihydro-2,2-dimethyl-5-fluorobenzofuran-7-yl)-1-piperazinyl]-1-butyl]-2-imidazolidinone,oxalate, 2mm, mp: 125–35° C. $^1$H NMR (δ, DMSO): 1.00–1.80 (m, 14H), 1.40 (s, 6H), 2.95 (s, 2H), 3.00–3.50 (m, 17H), 6.50 (dd, 1H), 6.65 (dd, 1H).

1—Cyclopentyl-3-[6-[4-(2,3-dihydro-2,2-dimethylbenzofuran-7-y 1)-1-piperazinyl]-1-hexyl]-2-imidazolidinone,oxalate, 2nn, mp: 132–34° C. $^1$H NMR (δ, DMSO): 1.15–1.75 (m, 14H), 1.40 (s, 6H), 2.95 (s, 2H), 2.95–3.10 (m, 4H), 3.15–3.45 (m, 12H), 4.00–4.15 (m, 1H), 6.65 (d, 1H), 6.75 (t, 1H), 6.85 (d, 1H).

1-[2-[4-(5—Chloro-2,3-dihydro-3,3-dimethyl)-7-benzofuranyl)-1-piperazinyl]ethyl]-3-cyclopentyl-2-imidazolidinone, oxalate, 2oo, mp: 104–7° C. $^1$H NMR (CDCl$_3$) δ 1.25 (s, 6H), 1.40–1.75 (m, 8H), 3.00 (t, 2H), 3.05–3.15 (m, 4H), 3.20–3.35 (m, 8H), 3.40 (t, 2H), 4.00–4.15 (m, 1H), 4.25 (s, 2H), 6.70 (d, 1H), 6.90 (d, 1H).

1-[6-[4-(5—Chloro-2,3-dihydro-3,3-dimethyl)-7-benzofuranyl)-1-piperazinyl]-1-hexyl]-3-cyclopentyl-2-imidazolidinone, oxalate, 2pp, mp: 125–27° C. $^1$H NMR (CDCl$_3$) δ 1.25 (s, 6H), 1.20–1.75 (m, 16H), 2.95 (t, 2H), 3.00 (t, 2H), 3.10–3.40 (m, 12H), 4.00–4.15 (m, 1H), 4.25 (s, 2H), 6.70 (d, 1H), 6.90 (d, 1H).

1-[3-[4-(7—Chloro-2,3-dihydro-2,2-dimethyl)-4-benzofuranyl)-1-piperazinyl]-1-propyl]-3-cyclohexyl-2-imidazolidinone, oxalate, 2qq, mp: 123–33° C. $^1$H NMR (CDCl$_3$) δ0.95–1.50 (m, 5H), 1.45 (s, 6H), 1.50–1.65 (m, 3H), 1.65–1.90 (m, 4H), 2.85–3.30 (m, 18H), 3.35–3.50 (m, 1H), 6.45 (d, 1H), 7.10 (d, 1H).

Example 3
1-(1,4—Benzodioxan-5-yl)-4-(3-cyclohexylthio-1-propyl) piperazine S-oxide, oxalate, 3a A solution of 1-(1,4-benzodioxan-5-yl)-4-(3-cyclohexylthio-1-propyl)piperazin (7 g) in tetrahydrofuran (70 ml) was cooled to 0° C. followed by portionwise addition of m-chloroperbenzoic acid (6.4 g) keeping the temperature at 0° C. After stirring for 3 h at 0° C. aqueous sodium carbonate (20% solution, 100 ml) was added. The phases were separated and the aqueous phase was extracted with methylene chloride. The combined organic phases was concentrated in vacuo and the resulting oil applied to a silica gel column (eluent: ethyl acetat/methanol/diethylamine=88:8:4). The title compound crystallized as the oxalate salt from an acetone/methanol mixture by addition of oxalic acid. Yield: 1.5 g, mp: 113–15° C.$^1$H NMR (δ, DMSO): 1.00–1.50 (m, 6H), 1.55–2.20 (m, 7H), 2.55–2.95 (m, 4H), 2.95–3.35 (m, 8H), 4.15–4.35 (m, 4H), 6.50 (d, 1H), 6.55 (d, 1H), 6.75 (t, 1H).

Example 4
1-[3-[4-(1,4—Benzodioxan-5-yl)-1-piperazinyl]-1-propyl]-3-benzyl-2-imidazolidinone, hydrochloride, 4a A solution of 1-[3-[4-(1,4-benzodioxan-5-yl)-1-piperazinyl]-1-propyl]-2-imidazolidinone (prepared from 1-(1,4-benzodioxan-5-yl)piperazin and 1-(3-chloro-1-propyl)-2-imidazolidinone by the method described in EXAMPLE 2) (2.5 g) and benzaldehyde (2.3 g) in glacial acetic acid (30 ml) was treated portionwise with sodium borohydride (0.6 g) keeping the temperature at 10° C. After stirring for 40 min. at room temperature additional benzaldehyde (2.3 g) and sodium borohydride (0.6 g) was added and the mixture stirred for 16 h at room temperature. Removal of solvent in vacuo gave a heavy oil which was applied to a silica gel column (eluent: ethyl acetate/ethanol/triethylamine=10:1:1). The title compound was isolated as a viscous oil which crystallized as the hydrochloride from an acetone/ether mixture by addition of an ether solution of dry HCl. Yield: 2.8 g, mp: 181–91° C. $^1$H NMR ($\delta$, DMSO): 1.90–2.10 (m, 2H), 3.00–3.25 (m, 10H), 3.30 (t, 2H), 3.35–3.65 (m, 4H), 4.20 (s, 4H), 4.25 (s, 2H), 6.50 (d, 1H), 6.55 (d, 1H), 6.75 (t, 1H), 7.00 (b, 2H), 7.20–7.40 (m, 5H).

In a similar manner were also prepared:

1-[3-[4-(1,4—Benzodioxan-5-yl)-1-piperazinyl]-1-propyl]-3-ethyl-2-imidazolidinone, hydrochloride, 4b, mp: 240–43° C. $^1$H NMR ($\delta$, DMSO): 1.00 (t, 3H), 1.85–2.05 (m, 2H), 2.95–3.35 (m, 14H), 3.35–3.65 (m, 4H), 4.25 (s, 4H), 6.35 (b, 2H), 6.50 (d, 1H), 6.55 (d, 1H), 6.75 (t, 1H).

1-[3-[4-(1,4—Benzodioxan-5-yl)-1-piperazinyl]-1-propyl]-3-cyclohexyl-2-imidazolidinone, hydrochloride, 4c, mp: 189–200° C. $^1$H NMR ($\delta$, DMSO): 0.95–1.50 (m, 5H), 1.50–1.65 (m, 3H), 1.65–1,85 (m, 2H), 1.90–2.10 (hep, 2H), 3.00–3.35 (m, 12H), 3.35–3.60 (m, 5H), 4.15–4.30 (m, 4H), 6.45–6.60 (m, 2H), 6.75 (t, 1H).

Example 5

1-[3-[4-(1,4—Benzodioxan-5-yl)-1-piperazinyl]-1ethyl]-1,3-dihydro-3-(4-fluorophenyl)-2-imidazolone, hydrochloride, 5a A solution of 1-(1,4-benzodioxan-5-yl)piperazin (11 g) and triethylamine (7 ml) in N-methyl-2-pyrrolidinone was treated dropwise with chloroacetonitrile (4.5 g). After stirring for 2 h at 100° C. the mixture was poured onto ice and extracted with ethyl acetate. The organic phase was washed with water, dried over magnesium sulfate, filtered, and concentrated in vacuo. The product, 1-(1,4-benzodioxan-5-yl)-4-cyanomethylpiperazine, was obtained as an oil (17.4 g) which was sufficiently pure for use in the next step.

A suspension of lithium aluminium chloride (8.2 g) in dry ether (170 ml) was treated dropwise with a solution of aluminium chloride (8.2 g) in ether (170 ml) under cooling. After stirring for half an hour at room temperature a solution of 1-(1,4-benzodioxan-5-yl)-4-cyanomethylpiperazine (9.4 g) in dry tetrahydrofuran (250 ml) was added dropwise at 15° C. After reflux for 1.5 h the mixture was cooled and conc. sodium hydroxide solution (40 ml) was added dropwise. Filtration and removal of solvent in vacuo gave an oil which was dissolved in methylene chloride and dried over magnesium sulfate. Removal of solvent in vacuo gave 1-(2-amino-1-ethyl)-4-(1,4-benzodioxan-5-yl) piperazine (9.1 g) as a viscous oil.

A mixture of 1-(2-amino-1-ethyl)-4-(1,4-benzodioxan-5-yl)piperazine (9.1 g), bromoacetaldehyde dimethylacetale (6.5 g), potassium iodide (0.5 g), and potassium carbonate (4.8 g) in 1,4-dioxan (200 ml) was refluxed for 16 h. Water was added followed by extraction with ethyl acetate. The organic phase was concentrated in vacuo leaving an oil which was applied to a silica gel column (eluent: ethyl acetate/methanol=1:3). The product, 1-(1,4-benzodioxan-5-yl)-4-[2-(2,2-dimethoxy-1-ethylamino)-1-ethyl]piperazine, was obtained as an oil (4.7 g).

A solution of 1-(1,4-benzodioxan-5-yl)-4-(2-(2,2-dimethoxy-1-ethylamino)-1-ethyl)piperazine (2.3 g) and 4-fluorophenyl isocyanate (0.9 g) in methylene chloride (100 ml) was refluxed for 2 h. Removal of solvent in vacuo gave an oil which was purified on a silica gel column (eluent: ethyl acetate/methanol=3:1). The product, 1-(1,4-benzodioxan-5-yl)-4-(2-(N-2,2-dimethoxy-1-ethyl)-N-(4-fluorophenylaminocarbonyl)-amino)-1-ethyl)piperazine, was obtained as a solid (2.5 g).

A solution of 1-(1,4-benzodioxan-5-yl)-4-(2-(N-(2,2-dimethoxy-1-ethyl)-N-(4-fluorophenylaminocarbonyl)amino)-1-ethyl)piperazine (2.5 g) and 3 M hydrochloric acid (2.5 ml) in ethanol (50 ml) was stirred at room temperature for 72 h. The title compound was collected by filtration as the hydrochloride. Yield: 1.2 g, mp: 301–5° C. $^1$H NMR ($\delta$, DMSO): 3.00–3.60 (m, 10H), 4.05 (t, 2H), 4.20–4.35 (m, 4H), 6.55 (t, 2H), 6.75 (t, 1H), 6.80 (d, 1H), 7.00 (d, 1H), 7.25 (t, 2H), 7.65–7.80 (m, 2H).

In a similar manner was also prepared:

1-[3-[4-(1,4—Benzodioxan-5-yl)-1-piperazinyl]-ethyl]-1,3-dihydro-3-phenyl-2-imidazolone, hydrochloride, 5b, mp: 295–300° C. $^1$H NMR ($\delta$, DMSO): 3.00–3.60 (m, 10H), 4.05 (t, 2H), 4.20–4.30 (m, 4H), 6.50 (t, 2H), 6.70 (t, 1H), 6.80 (d, 1H), 7.00 (d, 1H), 7.20 (t, 1H), 7.45 (t, 2H), 7.70 (d, 2H).

Example 6

1-(2—Cyclohexylsulfonyl-1-ethyl)-4-(2,3-dihydrobenzofuran-7-yl)piperazine, maleate, 6a A solution of 2-cyclohexylsulfonylethanol (22 g) and triethylamine (30 ml) in methylene chloride (200 ml) was treated dropwise with a solution of methanesulfonyl chloride (15 ml) in methylene chloride (100 ml) at 10° C. After stirring for 2 h at room temperature the mixture was washed with water, dried over magnesium sulfate and concentrated in vacuo leaving the product, cyclohexyl vinyl sulfone, as an oil (19 g).

A solution of cyclohexyl vinyl sulfone (2.4 g) and 1-(2,3-dihydrobenzofuran-7-yl)piperazine (2.5 g)3in methylene chloride (50 ml) was stirred at room temperature for 16 h. Removal of solvent in vacuo left an oil which was applied to a silica gel column (eluent: ethyl acetate/methanol/diethylamine=97:2:1). The title compound was obtained as an oil which crystallized as the maleate salt from acetone by addition of maleic acid. Yield: 3.4 g, mp: 178–79° C. $^1$H NMR ($\delta$, DMSO): 1.00–1.50 (m, 5H), 1.60–1.70 (m, 1H), 1.75–1.90 (m, 2H), 2.00–2.15 (m, 2H), 3.00–3.35 (m, 13H), 3.45 (t, 2H), 4.50 (t, 2H), 6.10 (s, 2H), 6.65 (d, 1H), 6.75 (t, 1H), 6.85 (d, 1H).

Example 7

1—Cyclopentyl-3-[2-[4-[1-(4-fluorophenyl)-4-indolyl]-1-piperazinyl]ethyl]-2-imidazolidinone, oxalate, 7a A mixture of 2y (1.3 g), 4-fluoroiodobenzene (2.0 g), cupper powder (0.2 g), potassium carbonate (0.8 g) in N-methyl-pyrrolidinone (20 ml) was kept at 170° C. under stirring for 5 h. After cooling the reaction mixture was filtered and water (200 ml) added followed by extraction with dichloromethane (2×100 ml). Removal of solvent in vacuo and purification by flash chromatography (silica gel, ethyl acetate/triethylamine 95:5) gave the free base as a solid (0.8 g). The title oxalate salt crystallized by addition of oxalic acid to an ethanol solution of the base. Yield: 0.7 g, mp: 210–12° C. $^1$H NMR ($\delta$, DMSO): 1.40–1.75 (m, 8H), 3.10 (t, 2H), 3.20–3.45 (m, 16H), 4.05–4.15 (m, 1H), 6.65 (d, 1H), 6.70 (dd, 1H), 7.05–7.15 (m, 2H), 7.40 (t, 2H), 7.55–7.65 (m, 3H).

Example 8

4-[4-[2-(3—Cyclopentyl-2-imidazolidinon-1-yl)ethyl]-1-piperazinyl]-2-benzofuranylcarboxamide, hydrochloride, monohydrate, 8a A solution of 2cc (1.0 g) in a mixture of conc. ammonia (50 ml) and tetrahydrofuran (25 ml) was kept at 50° C. for 48 h. Extraction with ether (3×50 ml), drying over magnesium sulfate, and removal of solvent in vacuo gave the free base as an oil. Addition of an etheral solution of HCl to an ethanol/heptane solution of the base gave the title hydrochloride salt. Yield: 0.5 g, mp: 166–70° C. $^1$H NMR ($\delta$, DMSO): 1.40–1.75 (m, 8H), 3.20–3.85 (m, 16H), 4.05–4.15 (m, 1H), 6.80 (d, 1H), 7.25 (d, 1H), 7.35 (t, 1H), 7.65 (b, 1H), 7.80 (s, 1H), 8.10 (b, 1H), 11.15 (b, 1H).

Example 9

1—Cyclopentyl-3-[2-[4-(7-indolinyl)-1-piperazinyl]ethyl]-2-imidazolidinone, 9a

A solution of 2u (1.3 g) in trifluoroacetic acid was treated portionwise over 3 h with sodium cyanoborohydride (0.6 g) at room temperature. After additional stirring for 0.5 h the mixture was poured onto ice followed by extraction with ethyl acetate (3×100 ml). Removal of solvent in vacuo and purification by chromatography (silica gel, ethyl acetate/triethylamine 96:4) gave the title compound as a crystalline material. Yield: 0.2 g, mp: 130–32° C. $^1$H NMR ($\delta$, CDCl$_3$): 1.40–1.85 (m, 8H), 2.55 (t, 2H), 2.55–2.70 (m, 4H), 2.95–3.05 (m, 4H), 3.05 (t, 2H), 3.20–3.45 (m, 6H), 3.55 (t, 2H), 4.25 (hep, 1H), 6.65–6.75 (m, 2H), 6.80–6.90 (m, 1H).

Example 10

1—Cyclohexyl-3-[4-[4-(2,3-dihydro-2,2-dimethylbenzofuran-7-yl)-1,2,3,6-tetrahydropyrid-1-yl]-1-butyl]-2-imidazolidinone, oxalate, 10a A mixture of 2,3-dihydro-2,2-dimethylbenzofuran (25 g) and tetramethylethylenediamine (46 g) in heptane (250 ml) was treated dropwise at room temperature with 1.6 M BuLi in hexane (250 ml). After stirring for 1.5 h at 30–40° C. the mixture was cooled to −40° C. and 1-benzyl-4-piperidinone (32 g) was added dropwise at −40° C. The reaction mixture was allowed to warm to room temperature during 3 h followed by quench with water. After concentrating the reaction mixture in vacuo dichloromethane (500 ml) was added followed by wash with water (3×500 ml). Removal of solvent in vacuo gave an oil which was purified by flash chromatography (silica gel, heptane/ethyl acetate/triethylamine 50:48:2) giving an oil. Addition of heptane gave the product, 7-(1-benzyl-4-hydroxy-4-piperidinyl)-2,3-dihydro-2,2-dimethylbenzofuran as a solid (11 g).

The obtained solid was dissolved in trifluoroacetic acid (150 ml) and refluxed for 1 h. The mixture was poured onto ice followed by basification with conc. NaOH. Extraction with dichloromethane (3×100 ml) and removal of solvent in vacuo gave an oil which was applied to a silica gel flash column (eluent: ethyl acetate/heptane/triethylamine 50:48:2) giving 7-(1-benzyl-1,2,3,6-tetrahydropyrid-4-yl)-2,3-dihydro-2,2-dimethylbenzofuran as an oil (5.0 g).

The product was dissolved in trichloroethane (15 ml) and added dropwise to ethyl chloroformate (20 ml) at reflux temperature. After reflux for 1 h the volatiles were removed in vacuo leaving crude 7-(1-ethoxycarbonyl-1,2,3,6-tetrahydropyrid-4-yl)-2,3-dihydro-2,2-dimethylbenzofuran as an oil (4.5 g). The crude product was dissolved in ethanol (50 ml) and solid KOH (3 g) was added. After reflux for 20 h the mixture was poured into water followed by extraction with ethyl acetate. The organic phase was dried over magnesium sulfate and the solvent removed in vacuo leaving crude 2,3-dihydro-2,2-dimethyl-7-(1,2,3,6-tetrahydropyrid-4-yl)-benzofuran as an oil (2.9 g). The crude product was sufficiently pure for use in the final step. The obtained product was alkylated with 1-cyclohexyl-3-(4-chloro-1-butyl)-2-imidazolidinone (4.5 g) according to the method described in EXAMPLE 2 giving the free base of the title compound as an oil (2.7 g). The oxalate salt crystallized by addition of oxalic acid to an acetone solution of the base. Mp: 132–35° C. $^1$H NMR ($\delta$, DMSO): 0.95–1.80 (m, 14H), 1.40 (s, 6H), 2.65–2.75 (m, 2H), 2.95 (s, 2H), 3.00–3.10 (m, 5H), 3.20–3.25 (m, 4H), 3.25–3.35 (m, 3H), 3.40–3.50 (m, 1H), 6.30 (m, 1H), 6.80 (t, 1H), 7.10 (t, 2H).

Example 11

1—Cyclohexyl-3-[4-[4-(2,3-dihydro-2,2-dimethylbenzofuran-7-yl)-1-piperidinyl]-1-butyl]-2-imidazolidinone, oxalate, 11a A mixture of 10a, oxalate (1.0 9) and 5% Pd/C (0.2 g) in ethanol (20 ml) was kept under a hydrogen atmosphere at 4 atm. of pressure for 36 h. Filtration, removal of solvent in vacuo and addition of acetone/ether gave the title compound as a crystalline solid. Yield: 0.5 g, mp: 150–54° C. $^1$H NMR ($\delta$, DMSO): 0.95–2.05 (m, 18H), 1.40 (s, 6H), 2.80–3.10 (m, 8H), 3.15–3.25 (m, 4H), 3.35–3.50 (m, 3H), 6.75 (t, 1H), 6.90 (d, 1H), 7.05 (d, 1H).

Example 12

1-[2-[4-(1,4—Benzodioxan-5-yl) -1-piperazinyl]ethyl]-3-(4-fluorophenyl) -2(3 H)-benzimidazolone, 12a A mixture of 1-(2-hydroxyethyl)benzimidazolone (J. Davoll, *J. Chem. Soc.*, 1960, 308) (9 g), 4-fluoroiodobenzene (23 g), potassium carbonate (8.0 g), cupper(I) iodide (1 g), and zinc oxide (0.5 g) in N-methyl-2(3H)-pyrrolidinone (100 ml) was kept at 155° C. for 4.5 h. After cooling water (500 ml) was added followed by extraction with ethyl acetate (3×200 ml). The organic phase was washed with water and saturated calcium chloride solution and dried over magnesium sulfate. Removal of solvent in vacuo gave an oil which was purified by chromatography (silica gel, ethyl acetate) giving 1-(4-fluorophenyl)-3-(2-hydroxyethyl)-2(3H)-benzimidazolone (2 g) as a solid, mp: 124–26° C.

The oil was dissolved in dichloromethane (60 ml) and thionyl chloride (10 ml) and dimethylformamide (0.5 ml) was added followed by reflux for 16 h. Removal of volatiles in vacuo gave 1-(2-chloroethyl)-3-(4-fluorophenyl)-2(3H)-benzimidazolone (2 g) as an oil.

The obtained chloride was treated with 1-(1,4-benzodioxan-5-yl)piperazine (2.4 g) according to the method described in EXAMPLE 2 giving the title compound as a crystalline material. Yield: 1.7 g, mp: 161–62° C. $^1$H NMR ($\delta$, CDCl$_3$): 2.55–2.65 (m, 4H), 2.70 (t, 2H), 2.85–2.95 (m, 4H), 4.05 (t, 2H), 4.15–4.25 (m, 4H), 6.35–6.50 (m, 2H), 6.70 (t, 1H), 6.95–7.20 (m, 3H), 7.30 (d, 1H), 7.40 (t, 2H), 7.55–7.65 (m, 2H).

Example 13

1-[4-[4-(1,4—Benzodioxan-5-yl)-1-piperazinyl]-1-butyl]-3-(4-fluorophenyl)-2(3H-benzimidazolone, 13a A solution of 1-(4-fluorophenyl)-3-(1-propen-2-yl)-2(3H-benzimidazolone (prepared by arylation of 1-(1-propen-2-yl)-2(3H)-benzimidazolone (J. Davoll, *J. Chem. Soc.*, 1960, 308) according to the method described in EXAMPLE 12) (5 g) in ethanol (100 ml) was treated with conc. hydrochloric acid (50 ml) at room temperature. After stirring for 1.5 h water (150 ml) was added. The resulting precipitate was collected by filtration and dried. Yield: 4 g of 1-(4-fluorophenyl)-2(3H)-benzimidazolone, mp: 209–10° C.

The 4 g of product was dissolved in tetrahydrofuran (100 ml) followed by addition of potassium tert-butoxide (3.0 g) during 5–10 min. After stirring for 10 min 1,4-dibromobutane (15 ml) was added followed by heating to 50° C. for 5 h. After filtration and removal of solvent the remaining oil was purified by column chromatography (silica gel, heptane, heptane/ethyl acetate 1:1). The product, 1-(4-bromo-1-butyl)-3-(4-fluorophenyl)-2-imidazolidinone, (5.0 g) was obtained as an oil.

Treatment of the oil (2.5 g) with 1-(1,4-benzodioxan-5-yl)piperazine (2.5 g) according to the method described in EXAMPLE 2 gave the title compound as a crystalline material. Yield: 1.9 g, mp: 145–47° C. $^1$H NMR ($\delta$, CDCl$_3$): 1.55–1.75 (m, 2H), 1.80–1.95 (m, 2H), 2.45 (t, 2H), 2.55–2.70 (m, 4H), 3.00–3.15 (m, 4H), 4.00 (t, 2H), 4.20–4.40 (m, 4H), 6.45–6.60 (m, 2H), 6.75 (t, 1H), 7.00–7.30 (m, 6H), 7.45–7.55 (m, 2H).

Example 14
1—Cyclopentyl-3-[2-[4-(2-phenylbenzofuran-7-yl)-1-piperazinyl]ethyl]-2-imidazolidinone, oxalate, 14a A mixture of 2ii (1.1 g), 5% Pd/C, glacial acetic acid (2 ml) and ethanol (100 ml) was kept under a hydrogen atmosphere at 4 atm. of pressure for 72 h. Filtration and removal of solvent in vacuo gave an oil which was dissolved in ethyl acetate (15 ml). Addition of oxalic acid gave the title compound. Yield: 0.5 g, mp: 182–83° C. $^1$H NMR ($\delta$, DMSO): 0.95–1.80 (m, 8H), 2.95–3.15 (m, 4H), 3.15–3.35 (m, 8H), 3.40–3.60 (m, 4H), 6.80 (d, 1H), 7.15 (t, 1H), 7.25 (d, 1H), 7.35–7.45 (m, 2H), 7.50 (t, 2H), 7.95 (d, 2H).

1—Cyclopentyl-3-[2-[4-(2,3-dihydro-3,3-dimethyl)-7-benzofuranyl)-1-piperazinyl]ethyl]-2-imidazolidinone, oxalate, 14b, mp: 94–98° C. $^1$H NMR (CDCl$_3$) $\delta$1.25 (s, 6H), 1.40–1.75 (m, 8H), 3.00 (t, 2H), 3.05–3.35 (m, 12H), 3.40 (t, 2H), 4.00–4.15 (m, 1H), 4.20 (s, 2H), 6.65–6.75 (m, 1H), 6.75–6.85 (m, 2H).

1—Cyclopentyl-3-[6-[4-(2,3-dihydro-3,3-dimethyl)-7-benzofuranyl)-1-piperazinyl]-1-hexyl]-2-imidazolidinone, oxalate, 14c, mp: 128–31° C. $^1$H NMR (CDCl$_3$) $\delta$1.25 (s, 6H), 1.20–1.75 (m, 16H), 2.95–3.10 (m, 4H), 3.15–3.40 (m, 12H), 3.95–4.10 (m, 1H), 4.20 (s, 2H), 6.65–6.75 (m, 1H), 6.75–6.90 (m, 2H).

1—Cyclohexyl-3-[3-[4-(2,3-dihydro-2,2-dimethyl)-4-benzofuranyl)-1-piperazinyl]-1-propyl]-2-imidazolidinone, oxalate, 14d, mp: 181–83° C. $^1$H NMR (CDCl$_3$) $\delta$0.95–1.45 (m, 5H), 1.35 (s, 6H), 1.50–1.65 (m, 3H), 1.65–1.90 (m, 4H), 2.80–3.00 (m, 4H), 3.00–3.30 (m, 14H), 3.40–3.55 (m, 1H), 6.35 (d, 1H), 6.40 (d, 1H), 7.00 (t, 1H).

Pharmacology

The compounds of Formula I have been tested according to established and reliable pharmacological methods for determination of the affinity to the 5-HT$_{1A}$ receptor and for determination of the efficacy of the compounds with respect to said receptor. The tests were as descibed in the following.

Inhibition of $^3$H—8—OH—DPAT Binding to Serotonin 5-HT$_{1A}$ Receptors in Rat Brain in vitro By this method the inhibition by drugs of the binding of the 5-HT$_{1A}$ agonist 3H—8—OH—DPAT (1 nM) to 5-HT$_{1A}$ receptors in membranes from rat brain minus cerebellum is determined in vitro. Accordingly, this is a test for affinity for the 5-HT$_{1A}$ receptor. The assay was performed as described by Hyttel et al., *Drug Dev. Res.* 1988, 15, 389–404.

Antagonism of the Discriminative Stimulus Properties Induced by 8—OH—DPAT in Rats This test is used to determine the 5-HT$_{1A}$ receptor antagonistic effect of a test compound in vivo. A related method is described by Tricklebank, M. D., et al, *Eur. J. Pharmacol,* 1987, 133, 47–56; Arnt, *J. Pharmacology & Toxicology,* 1989, 64, 165.

PROCEDURE

Male Wistar rats are trained to discriminate between 8—OH—DPAT (0.4 mg/kg, i.p., 15 min pretreatment) and physiological saline in operant chambers equipped with two response levers. Between the levers a dipper is placed, where water rewards (0.1 ml) are presented. The rats are water deprived for at least 24 h and work in a fixed ratio (FR) schedule (final FR=32).

Following 8—OH—DPAT administration, responding is reinforced only on a designated (drug) lever, whereas responding on the opposite lever has no consequences. Following saline administration, responding is reinforced on the lever opposite to the drug lever. Drug and saline trials alternate randomly between days. The level of discrimination accuracy is expressed as the per cent drug responses and is calculated as the number of correct responses×100 divided by the sum of the correct and incorrect responses before the first reward. The time to the first reward is also recorded as a measure of reaction time. When stable accuracy (mean correct responding=90%; individual rats at least 75% correct responding) is obtained test sessions are included between training days. Test compound is injected s.c. or p.o. at appropriate time before 8—OH—DPAT and the test begins 15 min after 8—OH—DPAT injection. The test trial is terminated when a total of 32 responses are made on either lever or when 20 min have elapsed. No reward is given and the rats have free access to water for 20–30 min after the test. The effects are expressed as per cent inhibition of drug responding. Only results from rats making at least 10 responses on one lever are included in data analysis. Furthermore, only test sessions in which at least half of the rats respond are included.

The per cent inhibition of drug response obtained for each dose of test compound is used to calculate ED$_{50}$ values by log-probit analysis.

Generalization to the Discriminative Stimulus Properties Induced by 8—OH—DPAT in Rats This test is used to determine the 5-HT$_{1A}$ receptor agonistic effect of a test compound in vivo. A related method is described by Tricklebank, M. D., supra; Arnt, J. *Pharmacology & Toxicology,* 1989, 64, 165.

PROCEDURE

The procedure is the same as for the antagonism test mentioned above, except that the test compound is substituted for 8—OH—DPAT and injected s.c. usually 30 min or 45 min, respectively, before beginning of the test.

The per cent drug responce obtained for each dose of test compound is used to calculate ED$_{50}$ values by log-probit analysis.

Inhibition of 5—MeO—DMT-lnduced 5-HT Syndrome in Rats

The so-called 5-HT syndrome is a characteristic pattern of behaviours which are induced by 5-HT agonists with effects on 5-HT, possibly 5-HT$_{1A}$ receptors (Smith, L. M. and Peroutka, S. J., *Pharmacol. Biochem. & Behaviour,*1986, 24, 1513; Tricklebank, M. et al, *Eur. J. Pharmacol.* 1985, 117, 15). This test is a test for determining the antagonist effects of a test compound on 5-HT$_{1A}$ receptors in vivo by measuring the ability to inhibit 5—MeO—DMT induced 5-HT syndrome.

PROCEDURE

Male Wistar rats (Mol:Wist) weighing 170–240 g are used. Test substance is injected s.c. before 5—MeO—DMT 5 mg/kg, s.c. Four rats are used for each dose. A control group pretreated with saline is included each test day. 10, 15 and 20 min later the rats are observed for presence of serotonin (5-HT) syndrome. The following symptoms are recorded: 1) forepaw treading ("piano playing"), 2) head weaving and 3) hindleg abduction. Furthermore, flat motility is scored. Each part of the syndrome is scored as follows: marked effect (score 2), weak syndrome (score 1) and no effect (score 0). The scores of the three observation periods are added. Thus the maximum obtainable score for four rats is 24. The effect of the test substance is expressed as percent inhibition relative to the control group.

The percent inhibition of the piano playing syndrome is used as the response and ED$_{50}$ value are calculated by log-probit analysis.

The test results are shown in the following Tables 1–3.

TABLE 1

3H 8-OH-DPAT BINDING DATA (IC$_{50}$ values in nM)

| Compound No. | IC$_{50}$ | Compound No. | IC$_{50}$ |
|---|---|---|---|
| 1a | 2.6 | 2ee | 43 |
| 1b | 7.8 | 2ff | 6.6 |
| 1c | 2.6 | 2gg | 2.8 |
| 1d | 190 | 2hh | 130 |
| 1e | 23 | 2ii | 300 |
| 1f | 1.1 | 2jj | 1.1 |
| 2a | 16 | 2kk | 5.7 |
| 2b | 18 | 2ll | 10 |
| 2c | 13 | 2mm | 1.7 |
| 2d | 17 | 2nn | 5.4 |
| 2e | 0.45 | 2oo | 44 |
| 2f | 54 | 2pp | 20 |
| 2g | 37 | 2qq | 300 |
| 2h | 28 | 3a | 1.8 |
| 2i | 30 | 4a | 18 |
| 2j | 53 | 4b | 40 |
| 2k | 15 | 4c | 19 |
| 2l | 72 | 5a | 11 |
| 2m | 12 | 5b | 12 |
| 2n | 3.2 | 6a | 220 |
| 2o | 51 | 7a | 51000 |
| 2p | 3.7 | 8a | 3.9 |
| 2q | 13 | 9a | 230 |
| 2r | 23 | 10a | 1.2 |
| 2s | 32 | 11a | 3.5 |
| 2t | 15 | 12a | 36 |
| 2u | 110 | 13a | 22 |
| 2v | 71 | 14a | 9.7 |
| 2x | 75 | 14b | 38 |
| 2y | 28 | 14c | 7.5 |
| 2z | 34 | 14d | 22 |
| 2aa | 11 | Buspirone | 41 |
| 2bb | 0.92 | Gepirone | 310 |
| 2cc | 83 | Ipsapirone | 17 |
| 2dd | 0.5 | Flesinoxane | 4 |

It is seen from Table 1 that most of the compounds of the present invention bind to the 5-HT$_{1A}$ receptor with affinities comparable to reference compounds such as buspirone, gepirone, and flesinoxane.

TABLE 2

8-OH-DPAT CUE DATA (ED$_{50}$ values in µmol/kg, s.c.)

| Compound No. | Antagonism | Agonism |
|---|---|---|
| 1a | >0.62 | 0.034 |
| 1b | NT | 0.099 |
| 1c | NT | 0.069 |
| 1e | >10 | see note a) |
| 1f | NT | 0.052 |
| 2a | >11 | 3.1 |
| 2b | 2.7 | >11 |
| 2c | >2.6 | 0.76 |
| 2d | 6.3 | see note b) |
| 2e | 6.1 | see note c) |
| 2f | NT | 40 |
| 2g | >11 | 1.6 |
| 2m | NT | 2.3 |
| 2n | NT | 0.13 |
| 2o | 23 | 27 |
| 2p | NT | 1.1 |
| 2y | 1.9 | NT |
| 2bb | NT | 0.036 |
| 3a | NT | 0.020 |
| 5a | NT | 1.8 |
| Buspirone | NT | 0.62 |
| Gepirone | NT | 0.81 |
| Ipsapirone | NT | 1.6 |
| Flesinoxane | NT | 0.38 | note a): partial agonist, 30–75% response at 0.04–10 µmol/kg
note b): partial agonist, 30–50% response at 0.08–19 µmol/kg
note c): partial agonist, 20–60% response at 0.6–2.4 µmol/kg It is seen from Table 2 that the compounds of the present invention both include agonists and antagonists as determined in the 8—OH—DPAT cue model.

TABLE 3

INHIBITION OF 5-MeO-DMT INDUCED 5-HT SYNDROME (ED$_{50}$ values in µmol/kg, s.c.)

| Compound No. | ED$_{50}$ |
|---|---|
| 1a | 2.3 |
| 1b | 9.5 |
| 1c | 12 |
| 1e | 5.1 |
| 1f | 0.47 |
| 2a | 6.6 |
| 2b | 8.9 |
| 2c | 15 |
| 2d | 10 |
| 2e | 4.7 |
| 2f | 28 |
| 2g | 10 |
| 2o | 9.0 |
| 2p | 4.2 |
| 2y | 2.7 |
| 2bb | 0.78 |
| 3a | 5.2 |
| 5a | 12 |
| Buspirone | 4.3 |
| Gepirone | 32 |
| Ipsapirone | 26 |
| Flesinoxane | >44 |

It is seen from Table 3 that the compounds of the present invention are antagonists in the 5—MeO—DMT inhibition test.

Furthermore, the compounds of the invention were tested with respect to affinity for the α$_1$ adrenoceptors and for the dopamine D$_2$ receptor by determining their ability to inhibit the binding of $^3$H-prazosin to α$_1$ adrenoceptors (Hyttel, J. et al, *J. Neurochem.*, 1985, 44, 1615; Skarsfeldt, T. et al, *Eur. J. Pharmacol.*, 1986, 125, 323) and the binding of $^3$H-spiroperidol to D$_2$ receptors (Hyttel et al, *J. Neurochem.*, 1985, 44, 1615).

Some of the compounds of the present invention showed high selectivity for the 5-HT$_{1A}$ receptor, while other compounds of the invention showed mixed binding profiles. A certain class of compounds within this invention showed high affinity to both 5-HT$_{1A}$ receptors and D$_2$ receptors. All the mentioned types of compounds are beneficial in the treatments of various diseases.

It is seen from the above tables 1, 2 and 3 that the present compounds have high affinities for the 5-HT$_{1A}$ receptor. Furthermore, it is seen that this series comprises compounds showing effects as partial agonists with medium to low efficacies. In particular, it is noted that some of the compounds show antagonistic effects in the 5—MeO—DMT test and very low efficacies in the 8—OH—DPAT cue test. Furthermore, some of the compounds show both high affinity to 5-HT$_{1A}$ and dopamine D$_2$ receptors and show high efficacy effects in the 8—OH—DPAT cue test.

Formulation Examples

The pharmaceutical formulations of the invention may be prepared by conventional methods in the art.

For example: Tablets may be prepared by mixing the active ingredient with ordinary adjuvants and/or diluents and subsequently compressing the mixture in a conventional tabletting machine. Examples of adjuvants or diluents comprise: corn starch, potato starch, talcum, magnesium stearate, gelatine, lactose, gums, and the like. Any other adjuvants or additives usually used for such purposes such as colourings, flavourings, preservatives etc. may be used provided that they are compatible with the active ingredients.

Solutions for injections may be prepared by dissolving the active ingredient and possible additives in a part of the solvent for injection, preferably sterile water, adjusting the solution to desired volume, sterilization of the solution and filling in suitable ampules or vials. Any suitable additive conventionally used in the art may be added, such as tonicity agents, preservatives, antioxidants, etc.

Typical examples of recipes for the formulation of the invention are as follows:

1) Tablets containing 5.0 mg of Compound 1a calculated as the free base:

| 1) Tablets containing 5.0 mg of Compound 1a calculated as the free base | |
|---|---|
| Compound 1a | 5.0 mg |
| Lactose | 60 mg |
| Maize starch | 30 mg |
| Hydroxypropylcellulose | 2.4 mg |
| Microcrystalline cellulose | 19.2 mg |
| Croscarmellose Sodium Type A | 2.4 mg |
| Magnesium stearate | 0.84 mg |
| 2) Tablets containing 0.5 mg of Compound 1f calculated as the free base | |
| Compound 1f | 0.5 mg |
| Lactose | 46.9 mg |
| Maize starch | 23.5 mg |
| Povidone | 1.8 mg |
| Microcrystalline cellulose | 14.4 mg |
| Croscarmellose Sodium Type A | 1.8 mg |
| Magnesium stearate | 0.63 mg |
| 3) Syrup containing per millilitre | |
| Compound 2bb | 2.5 mg |
| Sorbitol | 500 mg |
| Hydroxypropylcellulose | 15 mg |
| Glycerol | 50 mg |
| Methyl-paraben | 1 mg |
| Propyl-paraben | 0.1 mg |
| Ethanol | 0.005 ml |
| Flavour | 0.05 mg |
| Saccharin natrium | 0.5 mg |
| Water | ad 1 ml |
| 4) Solution for injection containing per millilitre | |
| Compound 2e | 0.5 mg |
| Sorbitol | 5.1 mg |
| Acetic acid | 0.08 mg |
| Water for injection | ad 1 ml |

What is claimed is:

1. A fused benzo compound having the formula

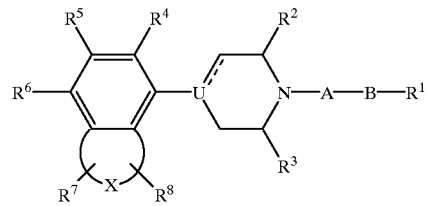

wherein A is a 2 to 6 membered spacer group selected from alkylene, alkenylene, and alkynylene which optionally may be branched chain when A is a 3 to 6 membered spacer, or straight chain, or a 3–7 membered cycloalkylene group, said spacer group being optionally substituted with aryl or hydroxy;

B is a polar divalent group selected from the group consisting of SO, $SO_2$, and a group having the formula,

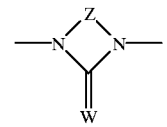

wherein W is O or S, and Z is selected from the group consisting of —$(CH_2)_n$—, wherein n is 2, —CH=CH—,

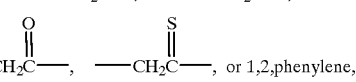, or 1,2,phenylene, said phenylene being optionally substituted with halogen or trifluoromethyl;

U is N; the dotted line designates an optional double bond; wherein X is selected from the group of divalent 4-membered groups consisting of

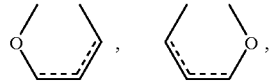

wherein the dotted lines indicate optional double bonds; thereby forming a heterocyclic ring fused with the benzene ring;

$R^1$ is alkyl, alkenyl, cycloalkyl, cycloalkenyl, phenyl, cycloalkylalkyl, cycloalkenylalkyl, cycloalkylalkenyl, cycloalkenylalkenyl, cycloalkylalkynyl, cycloalkenylalkynyl, phenylalkyl, or diphenylalkyl; wherein any alkyl group optionally may be substituted with one or two hydroxy groups, with the proviso that if Z is 1,2-phenylene, then $R^1$ is selected from phenyl and substituted phenyl; $R^2$ and $R^3$ are independently hydrogen, lower alkyl or they may be linked together, to form an ethylene or propylene bridge; $R^4$, $R^5$, and $R^6$ are independently selected from the group consisting of hydrogen, halogen, lower alkyl, hydroxy, lower alkylthio, lower alkylamino, di-lower-alkylamino, cyano, nitro, trifluoromethyl and trifluoromethylthio; $R^7$ and $R^8$ are independently selected from the group consisting of hydrogen, halogen, trifluoromethyl, lower alkyl, lower alkyl substituted with one or more hydroxy groups, aryl, cyano, —COOR$^9$ and —CONR$^{10}$R$^{11}$, R$^9$, R$_{10}$, and R$^{11}$ are hydrogen or lower alkyl; any phenyl group present optionally may be substituted with one or more substituents selected from the group consisting of halogen, lower alkyl, lower alkoxy, hydroxy, lower alkylthio, lower alkylsulfonyl, lower alkylamino, lower dialkylamino, cyano, trifluoromethyl and trifluoromethylthio; and pharmaceutically acceptable acid addition salts thereof.

2. A compound according to claim 1, wherein A is a 2 to 6 membered alkylene group.

3. A compound according to claim 1, wherein B is SO, SO$_2$, or a group of formula

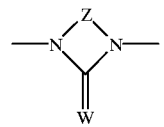

wherein W is O and Z is selected from —CH$_2$)$_n$—, wherein n is 2, —CH=CH— and 1,2-phenylene, said phenylene being optionally substituted with halogen or trifluoromethyl.

4. A compound according to claim 1, wherein R$^1$ is lower alkyl, phenyl, cycloalkyl or phenyl-alkyl.

5. A compound according to claim 4, wherein R$^1$ is lower alkyl, phenyl, substituted phenyl, C$_5$–C$_6$ cycloalkyl, adamantyl, phenyl-lower alkyl, said lower alkyl being optionally substituted.

6. A compound according to claim 1, wherein R$^2$ and R$^3$ are both hydrogen.

7. A compound according to claim 1, wherein R$^4$, R$^5$ and R$^6$ are each selected from the group consisting of hydrogen and halogen.

8. A compound according to claim 1, wherein R$^7$ and R$^8$ are independently selected from the group consisting of hydrogen, lower alkyl, —COOR$^9$ wherein R$^9$ is hydrogen or lower alkyl, and —CONH$_2$.

9. A pharmaceutical composition comprising at least one fused benzo compound according to claim 1, or a pharmaceutically acceptable acid addition salt thereof in a therapeutically effective amount and in combination with one or more pharmaceutically acceptable carriers or diluents.

* * * * *